(12) United States Patent
Duffy et al.

(10) Patent No.: US 11,801,137 B2
(45) Date of Patent: Oct. 31, 2023

(54) METHODS FOR ANCHORING A HEART VALVE PROSTHESIS IN A TRANSCATHETER VALVE IMPLANTATION PROCEDURE

(71) Applicant: Medtronic Vascular, Inc., Santa Rosa, CA (US)

(72) Inventors: Niall Duffy, Galway (IE); Joshua Dwork, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 919 days.

(21) Appl. No.: 16/784,614

(22) Filed: Feb. 7, 2020

(65) Prior Publication Data

US 2020/0246145 A1 Aug. 6, 2020

Related U.S. Application Data

(63) Continuation of application No. 15/541,461, filed as application No. PCT/US2016/018153 on Feb. 17, 2016, now Pat. No. 10,555,812.

(Continued)

(51) Int. Cl.
*A61F 2/24* (2006.01)
*A61B 17/068* (2006.01)
*A61B 17/064* (2006.01)

(52) U.S. Cl.
CPC ........ *A61F 2/2439* (2013.01); *A61B 17/0682* (2013.01); *A61F 2/2418* (2013.01);
(Continued)

(58) Field of Classification Search
CPC .... A61F 2/2439; A61F 2/2418; A61F 2/2436; A61F 2220/0016
See application file for complete search history.

(56) References Cited

U.S. PATENT DOCUMENTS 10,555,812 B2 * 2/2020 Duffy ................. A61F 2/2439
2007/0016287 A1 1/2007 Cartledge et al.
(Continued)

FOREIGN PATENT DOCUMENTS

WO 2007/097983 A1 8/2007
WO 2012/061809 A1 5/2012

OTHER PUBLICATIONS

International Search Report and the Written Opinion of the International Searching Authority dated Jun. 2, 2016 in International Application No. PCT/US2016/018153 (11 pp.).

*Primary Examiner* — Katherine M Rodjom
(74) *Attorney, Agent, or Firm* — Medler Ferro Woodhouse & Mills PLLC

(57) ABSTRACT

Methods of deploying and securing a heart valve prosthesis are disclosed. A heart valve prosthesis having a plurality of anchor guides is loaded within a catheter-based delivery device, wherein each of the anchor guides is releasably engaged by a respective elongate member and wherein tensioning of the elongate members aids in collapsing the prosthesis during loading. The delivery device is advanced via a transcatheter procedure to position the heart valve prosthesis at an implantation site. The heart valve prosthesis undergoes controlled deployment by controlling the release of tension on the elongate members. After deployment of the heart valve prosthesis, an anchor tool is advanced along at least one elongate guide member to the anchor guide associated therewith and positioned at a securement site. When the securement site is reached, an anchor clip is released from the anchor tool to secure the prosthesis to the heart.

19 Claims, 16 Drawing Sheets

Related U.S. Application Data

(60) Provisional application No. 62/117,013, filed on Feb. 17, 2015.

(52) U.S. Cl.
CPC ..... *A61B 17/064* (2013.01); *A61B 2017/0649* (2013.01); *A61F 2/2436* (2013.01); *A61F 2210/0014* (2013.01); *A61F 2220/0016* (2013.01)

(56) References Cited

U.S. PATENT DOCUMENTS

| | | | |
|---|---|---|---|
| 2009/0099640 A1* | 4/2009 | Weng | A61F 2/95 623/1.11 |
| 2012/0022640 A1 | 1/2012 | Gross et al. | |
| 2012/0323317 A1 | 12/2012 | Karapetian et al. | |
| 2014/0018906 A1 | 1/2014 | Rafiee | |
| 2016/0250051 A1* | 9/2016 | Lim | A61F 2/95 623/1.11 |

* cited by examiner

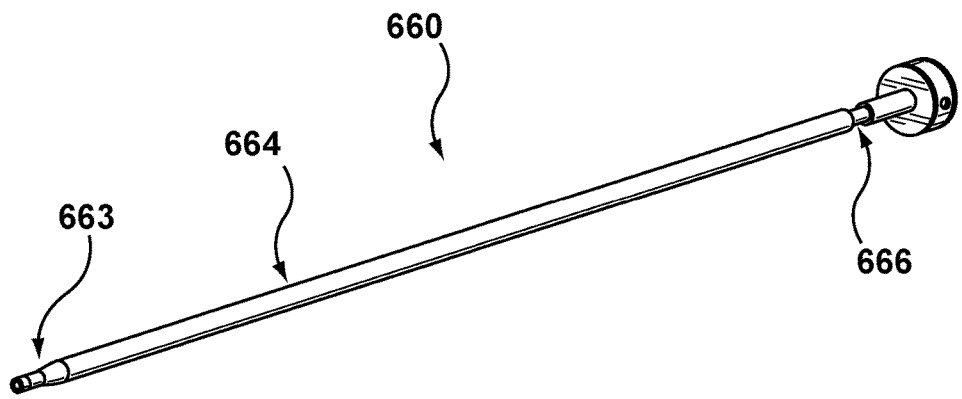
FIG. 6
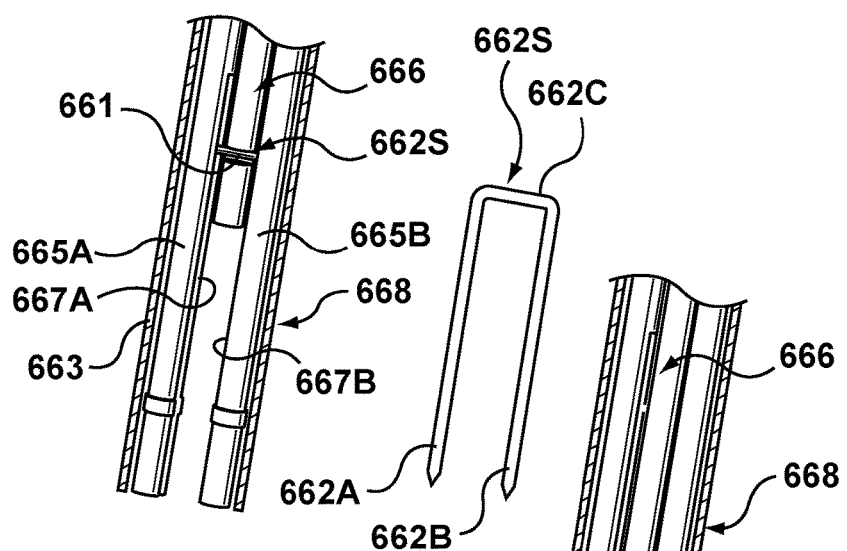
FIG. 6A
FIG. 6B
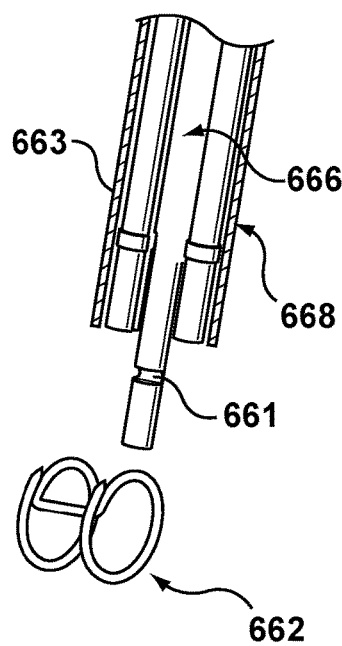
FIG. 6C

METHODS FOR ANCHORING A HEART VALVE PROSTHESIS IN A TRANSCATHETER VALVE IMPLANTATION PROCEDURE

CROSS-REFERENCE TO RELATED APPLICATIONS

This application is a continuation of prior U.S. application Ser. No. 15/541,461, filed Jul. 3, 2017, now U.S. Pat. No. 10,555,812, which is a national stage entry of PCT/US2016/018153, filed Feb. 17, 2016, which claims the benefit of U.S. Appl. No. 62/117,013, filed Feb. 17, 2015, the contents of which are incorporated by reference herein in their entirety.

FIELD OF THE INVENTION

The invention relates to methods for anchoring a heart valve prosthesis deployed within a native heart valve, or previously implanted heart valve prosthesis, in a transcatheter valve implantation procedure.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves situated between a respective atria and ventricle, while the aortic and pulmonary valves are semilunar valves situated between a respective ventricle and the aorta or pulmonary artery, respectively. Ideally, native leaflets of a heart valve move apart from each other when the valve is in an open position, and meet or "coapt" when the valve is in a closed position. Problems that may develop with valves include stenosis, in which a valve does not open properly, and/or insufficiency or regurgitation, in which a valve does not close properly. Stenosis and insufficiency may occur concomitantly in the same valve. The effects of valvular dysfunction vary, with regurgitation or backflow typically having relatively severe physiological consequences to the patient.

Recently minimally invasive approaches have been developed to facilitate catheter-based implantation of a valve prosthesis on a beating heart that are intended to obviate the need for the use of classical sternotomy and cardiopulmonary bypass. More particularly, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and thereafter advanced through the venous or arterial vasculature. Once the prosthetic valve is positioned at the treatment site, for instance within an incompetent native valve, the stent structure may be expanded to hold the prosthetic valve firmly in place.

A heart valve prosthesis employed with catheter-based, or transcatheter, procedures generally includes an expandable frame or stent that supports a valve body having a plurality of leaflets. The frame can be contracted during percutaneous transluminal delivery, and expanded upon deployment at or within the native valve or within a previously implanted prosthetic heart valve. Certain heart valve prostheses are configured to be initially provided in an expanded or uncrimped condition, then crimped or compressed about a balloon portion of a catheter. The balloon is subsequently inflated to expand and deploy the prosthetic heart valve. In other heart valve prostheses designs, the frame is formed to be self-expanding. With these systems, the heart valve prosthesis is reduced to a desired delivery diameter and held in that compressed state within a sheath for transluminal delivery. Retracting the sheath from covering the heart valve prosthesis allows the frame to self-expand toward its original, larger diameter and into apposition with the native valve site.

The actual shape or configuration of any particular prosthetic heart valve to be delivered in a transcatheter implantation procedure is dependent, at least to some extent, upon the native heart valve being replaced or repaired, i.e., mitral valve, tricuspid valve, aortic valve, or pulmonary valve. The frame must oftentimes provide and maintain a relatively complex shape in order to achieve desired fixation with the native anatomy and with self-expanding frame designs, the frame can experience significant, rapid radial expansion upon deployment from the sheath. Taken in combination, these design features can give rise to delivery concerns. A rapidly expanding frame having one section expanding to a substantially larger diameter than an adjacent section, for instance, can cause the prosthetic heart valve to spring off of the delivery device in a relatively uncontrolled fashion. This rapid deployment can, in turn, result in the valve body being improperly positioned. For example, exemplary prosthetic mitral valve designs can have an inflow diameter on the order of 60 mm, with an inflow section of the frame extending perpendicular, or nearly perpendicular, to an outflow section of the frame having an outflow diameter on the order of 30 mm. During transluminal delivery to the native mitral valve, the frame may be held in a compressed, nearly cylindrical shape with a diameter on the order of 12 mm. The inflow section is intended to self-expand into apposition with the atrium with the outflow section of the prosthetic mitral valve self-expanding into engagement with the native annulus. If a delivery system does not have a mechanism to control expansion of such a self-expanding frame, the inflow section of the frame can experience rapid, uncontrolled expansion upon deployment, such that the outflow section may seat improperly within the native mitral valve annulus, and such that the inflow section may fail to anchor sufficiently within the corresponding anatomy of the atrium.

Delivery systems that provide controlled deployment of a prosthetic heart valve having a self-expanding frame are shown and described in U.S. application Ser. No. 14/519,242 filed Oct. 21, 2014, which is incorporated by reference herein in its entirety. Such delivery systems may alleviate issues that can arise due to rapid, uncontrolled expansion of an inflow section of a self-expanding prosthetic heart valve, and also provide for recapture of the self-expanding prosthesis prior to full deployment. Although the delivery systems and techniques disclosed in the '242 application provide improvement over prior prosthetic heart valve delivery systems, there remains a need for continued improvement of such systems. For instance even after a self-expanding valve prosthesis is properly positioned, paravalvular leakage is still a concern as leakage may occur at the time of implantation or may occur after implantation due to changes in the native anatomy, such as elongation of the chordae tendinae, stretching of the native leaflets over time due to the stresses placed thereon by the functioning of a prosthetic mitral valve, and/or the migration of the papillary muscles over time due to the remodeling of the heart that over time. In order to address concerns regarding paravalvular leakage, embodiments hereof relate to a delivery system having the additional functionality of guiding a stapling or anchoring tool to an area of the heart valve prosthesis that may be in need of or may benefit from additional anchoring to tissue of the heart, such that the additional anchoring may further minimize relative movement between the prosthesis and the heart to prevent paravalvular leakage.

BRIEF SUMMARY OF THE INVENTION

Embodiments hereof are directed to methods of securing a heart valve prosthesis to a heart of a patient. Initially a heart valve prosthesis having an anchor guide is implanted or deployed via a transcatheter procedure within one of a native heart valve or a previously implanted heart valve prosthesis. The anchor guide of the implanted heart valve prosthesis has an elongate guide member releasably secured thereto with an end or ends of the elongate guide member extending externally of the patient from the implanted heart valve prosthesis. The elongate guide member so positioned is used to advance an anchor tool having an anchor clip loaded therein along the elongate guide member to the anchor guide of the heart valve prosthesis. Thereafter the anchor guide may be used to position the anchor tool at a securement site on the heart valve prosthesis, such that upon release of the anchor clip from the anchor tool at the securement site the heart valve prosthesis may be secured to the heart.

Embodiments hereof are also directed to methods of deploying and securing a heart valve prosthesis to a heart of a patient. In an embodiment, a heart valve prosthesis having a plurality of anchor guides is loaded within a heart valve delivery device, wherein each of the plurality of anchor guides is releasably engaged by a respective elongate member of a plurality of elongate members and wherein tensioning of the plurality of elongate members aids in collapsing the heart valve prosthesis during loading. The heart valve delivery device is advanced via a transcatheter procedure to position the heart valve prosthesis at an implantation site within one of a native heart valve or a previously implanted heart valve prosthesis. The heart valve prosthesis undergoes controlled deployment thereafter at the implantation site by controlling the release of tension on the plurality of elongate members. Once full deployment of the heart valve prosthesis is achieved, an anchor tool having an anchor clip loaded therein is advanced along at least one elongate guide member to the anchor guide associated therewith and positioned at a securement site on the heart valve prosthesis. When the securement site is reached, the anchor clip is released from the anchor tool at the securement site to secure the heart valve prosthesis to the heart.

In embodiments in accordance herewith, a securement site for an anchor clip may be determined by checking for leakage after the heart valve prosthesis is initially implanted or deployed. For instance, color Doppler imaging may be used to check for paravalvular leakage after the heart valve prosthesis is initially fully deployed into apposition with the heart, and if leakage is identified, than an anchor clip may be advanced to a securement site in the area of leakage. The anchor clip may then be secured to the prosthesis and the tissue of the heart at the securement site to thereby provide a better seal therebetween and to prevent further paravalvular leakage.

In embodiments in accordance herewith, securing an inflow or upstream area of a heart valve prosthesis with one or more anchor clips in accordance herewith prevents movement of a frame of the heart valve prosthesis which may in turn prevent the frame from failing over time due to fatigue. As well preventing movement of the heart valve prosthesis by using one or more anchor clips in accordance herewith may also prevent paravalvular leakage from developing after implantation.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 6 and 6A-6C depict an anchor tool in accordance with an embodiment hereof.

DETAILED DESCRIPTION OF THE INVENTION

Figure 1:
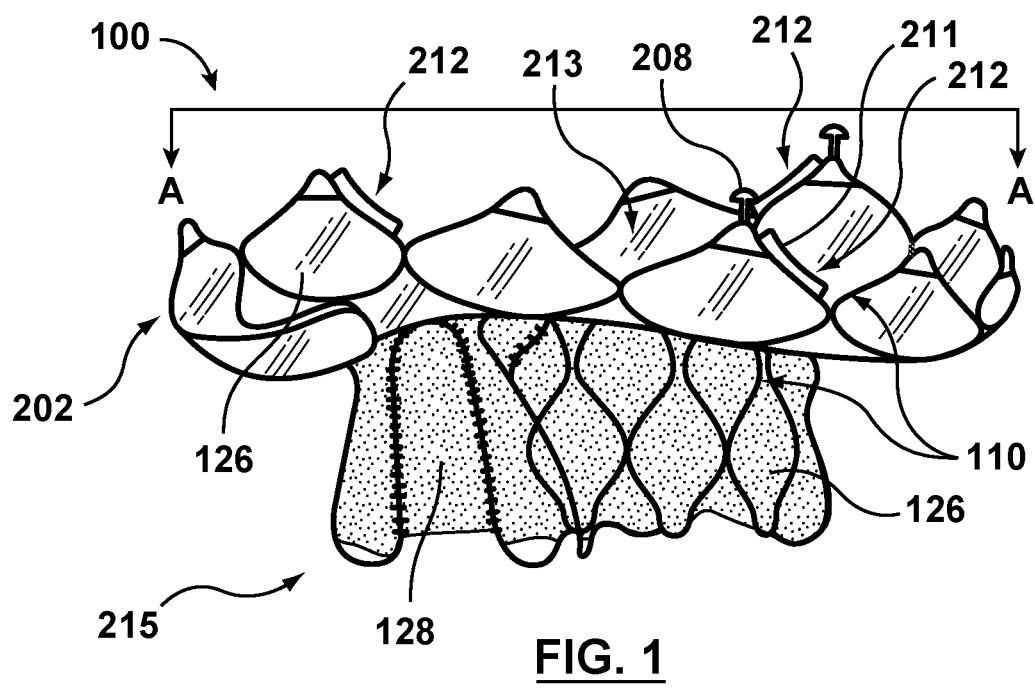
FIG. 1 is a side view of a heart valve prosthesis in accordance with an embodiment hereof shown in a deployed configuration.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. The following detailed description is merely exemplary in nature and is not intended to limit the invention or the application and uses of the invention. Although the description of embodiments hereof are in the context of delivery systems for delivering a prosthetic heart valve within a native mitral valve, the delivery systems of the invention can also be used in other areas of the body, such as for delivering a prosthetic heart valve within a native aortic valve, for delivering a prosthetic heart valve within a native pulmonic valve, for delivering a prosthetic heart valve within a native tricuspid valve, for delivering a venous valve, or for delivering a prosthetic heart valve within a failed previously-implanted prosthesis. Furthermore, there is no intention to be bound by any expressed or implied theory presented in the preceding technical field, background, brief summary or the following detailed description.

Heart valve prostheses for use with and/or forming a part of the various transcatheter systems, devices and methods described herein may assume a wide variety of different configurations, and can be specifically configured for replacing any of the four native heart valves of the human heart. Thus, a heart valve prosthesis useful with the systems, devices, and methods hereof may generally be used for replacement of a native aortic, mitral, pulmonic or tricuspid valve, or to replace a failed prosthetic heart valve, such as one that may have been prior implanted in the native aortic or mitral valve, for example.

In general terms, such a heart valve prosthesis includes a stent or frame defining an internal area within which a valve body or structure having two or more valve leaflets (tissue or synthetic) is secured. The frame of the heart valve prosthesis has a normal, expanded or deployed configuration that corresponds with implantation at a particular target site within the heart, and a compressed configuration for loading within a catheter-based delivery device. Generally, each stent or frame is a support structure that comprises a number of struts or wire segments arranged relative to each other to provide desired properties to the prosthetic heart valve, such as compressibility and strength. The frame is normally constructed to self-deploy or self-expand from the compressed, delivery configuration to the normal, expanded or deployed configuration when released from the delivery device. The term "self-expand" and other forms thereof are used in the following description and are intended to convey that the frame structure of a prosthetic heart valve used in embodiments hereof is shaped or formed from a material that can be provided with a mechanical memory to return the frame structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or scaffold frame by thermal treatment to achieve a spring temper in stainless steel, for example, or to set a shape memory in a susceptible metal alloy, such as Nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and polycyclooctene can be used separately or in conjunction with other shape memory polymers.

Figure 1A:
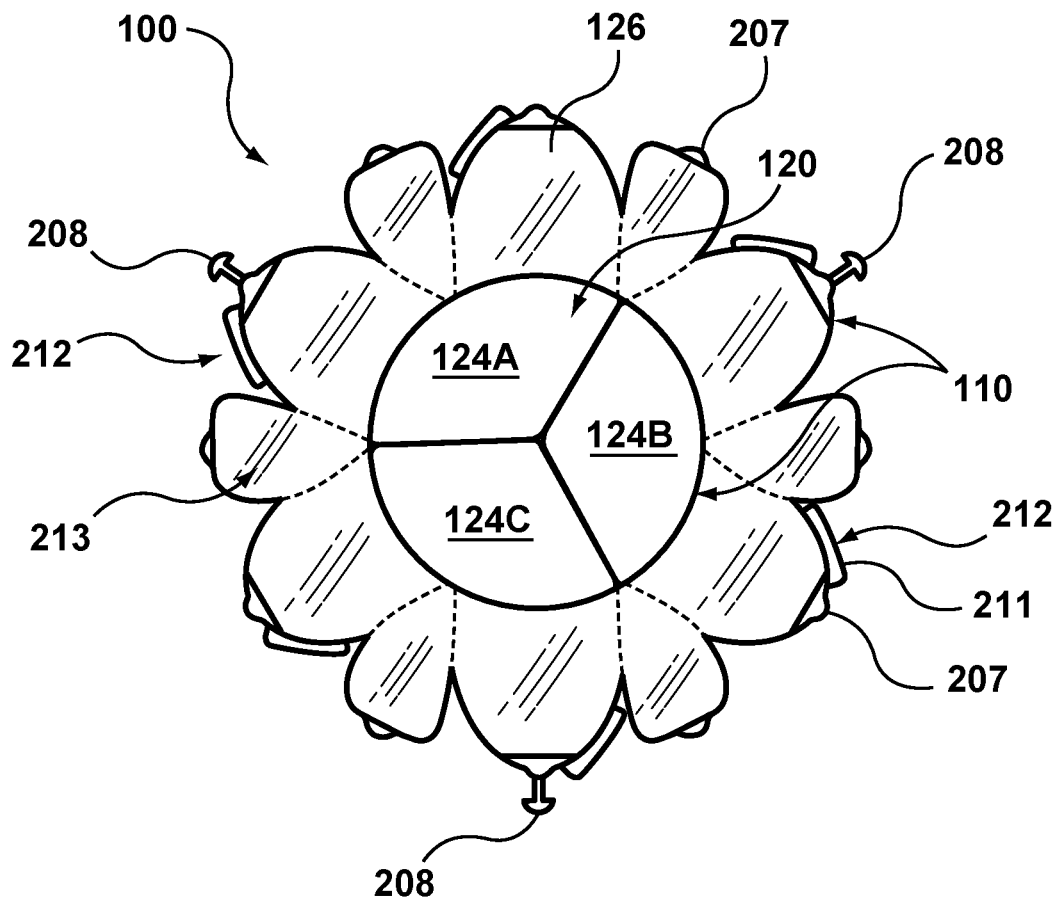
FIG. 1A is a top view of an inflow section or area of the heart valve prosthesis of FIG. 1 taken in the direction of line A-A therein.
Figure 2:
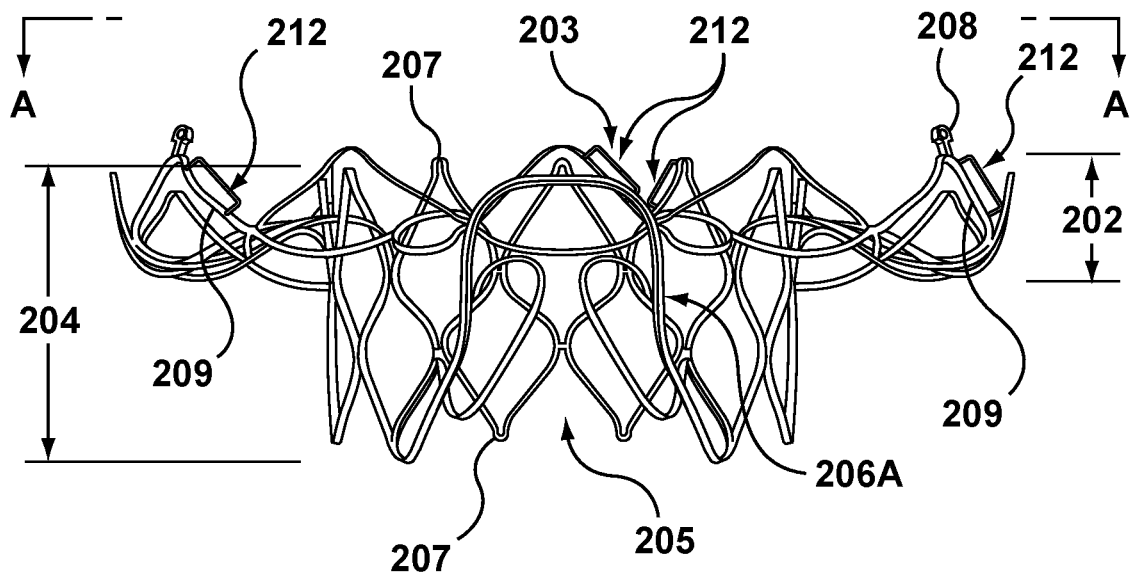
FIG. 2 is a side view of a frame of the heart valve prosthesis of FIG. 1 in an expanded state.
Figure 2A:
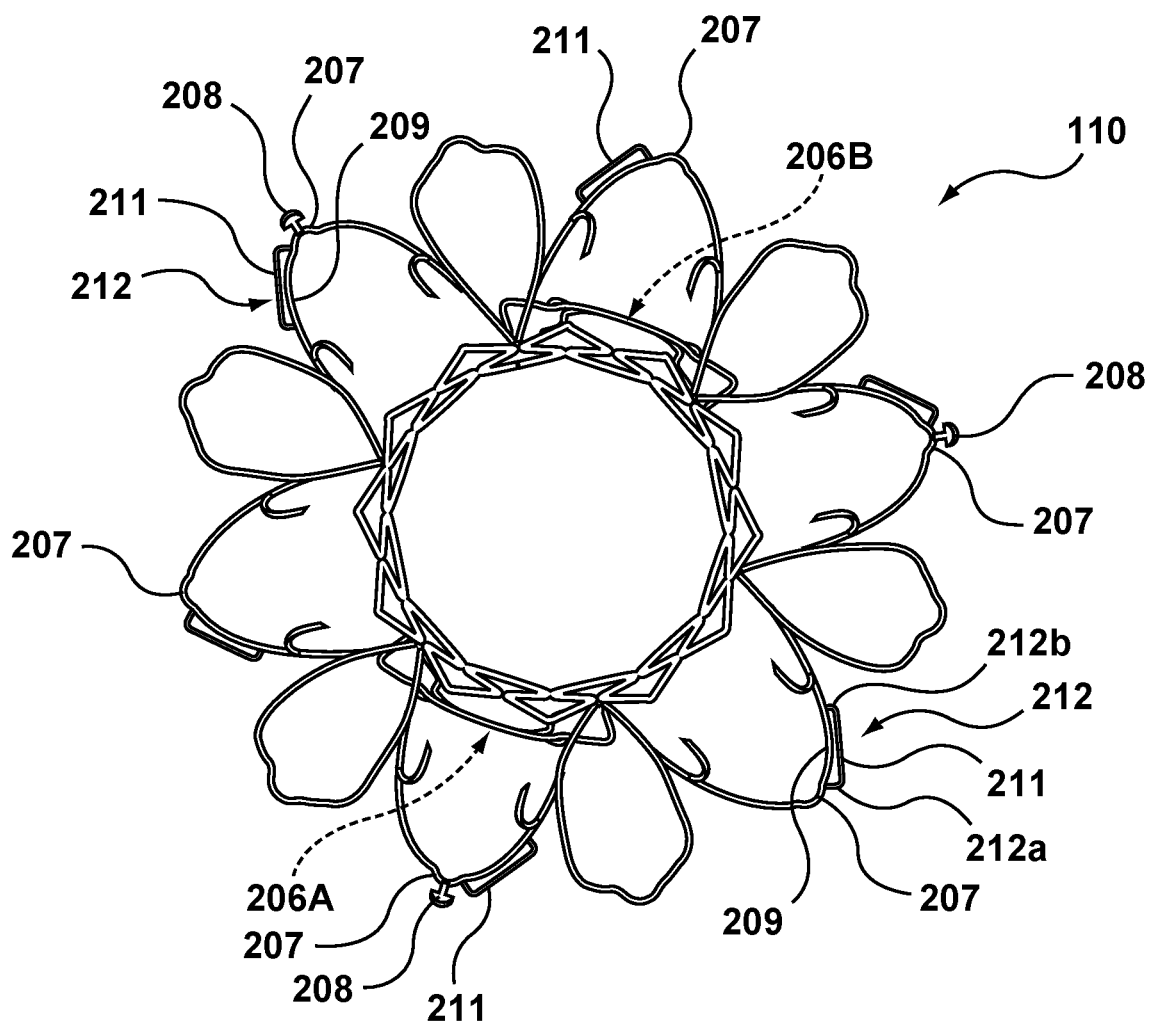
FIG. 2A is a top view of an inflow section or portion of the frame of FIG. 2 taken in the direction of line A-A therein.

FIGS. 1 and 1A illustrate an embodiment of a heart valve prosthesis 100 for use with the systems, devices and methods described herein, with FIGS. 2 and 2A depicting a self-expanding frame 110 of heart valve prosthesis 100 separated therefrom for illustrative purposes. More particularly, FIG. 1 is a side view of heart valve prosthesis 100 shown in a deployed configuration for use in treating a mitral valve in accordance with an embodiment hereof, with FIG. 1A being a top view of an inflow section or area of prosthesis 100 taken in the direction of line A-A in FIG. 1. Prosthesis 100 includes a valve component 120 attached within an interior of a frame or support structure 110. Valve component 120 is a one-way tricuspid replacement valve having first, second and third valve leaflets 124A, 124B, 124C. In another embodiment, valve component 120 may be a one-way bicuspid replacement valve having two valve leaflets. Valve leaflets 124A, 124B, 124C are sutured or otherwise securely and sealingly attached to an interior surface of frame 110 and/or to graft material 126, which encloses or lines various portions of frame 110. In embodiments in accordance herewith, graft material 126 secured to frame 110 within an inflow area of prosthesis 100 aids in sealing and graft material 126 secured to frame 110 proximate an outflow area of prosthesis 100 provides a tent-like or hammock structure 128, which functions to reduce or eliminate interaction between frame 110 and the chordae tendinae when prosthesis 100 is implanted within a native mitral valve.

FIGS. 2 and 2A illustrate frame 110 in a deployed configuration removed from a remainder of prosthesis 100, with FIG. 2 being a side view of frame 110 and FIG. 2A being a top or inflow view of frame 110 taken in the direction of line A-A in FIG. 2. Frame 110 may be a unitary structure that defines an inflow portion 202, a valve-retaining tubular portion 204 and a pair of support arms 206A, 206B. In embodiments in accordance herewith, frame 110 may be formed to be self-expanding and therefore can be forced and constrained into a compressed, tubular condition for loading within a catheter-based delivery system with shape memory to self-expand and return to its natural, expanded condition shown in FIG. 2 upon removal of the constraining force(s) of the delivery system. In embodiments hereof, self-expanding frame 110 may be configured to be compressed to a diameter on the order of 12 mm by the delivery system, and when released therefrom may be configured to self-expand to a natural, expanded condition that includes inflow portion 202 having a diameter on the order of 60 mm.

A first or inflow end 203 and a second or outflow end 205 of frame 110 are generally defined by a plurality of respective crowns 207, and optionally may include eyelets 208 for attachment to a delivery system. Inflow portion 202 of frame 110 includes or has attached thereto one or more anchor guides 212. In the embodiment shown in FIGS. 1, 1A, 2 and 2A, anchor guides 212 are a plurality of rails 211 attached to respective struts 209 of inflow portion 202. In an embodiment, a rail 211 may extend parallel to or substantially parallel to its corresponding strut 209 with a first end of the rail being disposed adjacent to a respective crown 207 and a second end of the rail being disposed along the corresponding strut 209. For instance with reference FIG. 2A, a first end 212a of rail 211 is disposed adjacent to crown 207 and a second end 212b of rail 211 is spaced from crown 207 to be disposed along strut 209. The guide rail 211 so shaped and positioned permits an associated tether or elongate member 338 to sit at an apex of the associated or corresponding crown 207 during controlled release and recapture of the heart valve prosthesis and permits the associated tether or elongate member 338 to slide down the rail to an anchor securement site or location when desired, as described in detail below.

When frame 110 is in the deployed configuration shown in FIGS. 2 and 2A, inflow portion 202 radially extends from valve-retaining tubular portion 204 with rails 211 upwardly extending therefrom. In addition, support arms 206A, 206B that are disposed at circumferentially spaced apart locations of outflow end 205 of valve-retaining tubular portion 204 extend toward inflow end 203 therefrom. With reference to FIGS. 1 and 1A that shows heart valve prosthesis 100 in the deployed configuration, rails 211 extend upwardly or away from inflow portion 202 to be disposed above and free of graft material 126. The functionality and alternate embodiments of anchor guides in accordance herewith are described in further detail below.

When prosthesis 100 is implanted within a native mitral valve, inflow portion 202 of frame 210 is configured to engage an area of the left atrium that surrounds the native mitral valve, valve-retaining tubular portion 204 of frame 210 is configured to axially extend through the native mitral valve and thusly situates valve component 120 within the mitral valve annulus, and support arms 206A, 206B are configured to capture respective valve leaflets of the mitral valve and to secure them within the left ventricle without obstructing the outflow area of prosthesis 100 or the left ventricular outflow tract. As well anchor guides, such as rails 212, are situated to be accessible from an inflow end 213 of prosthesis 100 as described in detail below.

With the above understanding of heart valve prosthesis 100, an embodiment of a catheter-based delivery device 330 for percutaneously delivering a valve prosthesis in accordance herewith is shown in simplified form in FIGS. 3 and 3A-3E. Delivery device 330 is a delivery catheter sized for transluminal delivery of heart valve prosthesis 100 to a target site within a native heart valve. Accordingly, delivery device 330 and heart valve prosthesis 100 form a system for performing a transcatheter procedure on a defective heart valve of a patient, and delivery device 330 is configured to provide a suitable compressed, delivery configuration of heart valve prosthesis 100 for transluminal delivery. Delivery device 330 includes a delivery sheath assembly 332, an inner shaft assembly 334, a hub assembly 336, one or more tethers 338, and a handle assembly 340. Details of the various assemblies that comprise delivery device 330, and variations thereof, may be found in U.S. application Ser. No. 14/519,242 filed Oct. 21, 2014, which is incorporated by reference herein in its entirety. Tethers 338 are also referred to herein as elongate members and elongate guide members, and are used after implantation of the heart valve prosthesis for guiding an anchor tool to an anchor guide as discussed below. In accordance with embodiments hereof, tethers/elongate guide members 338 may be formed from an elongate suture, thread, thin wire, or other flexible, elongate body.

Figure 3:
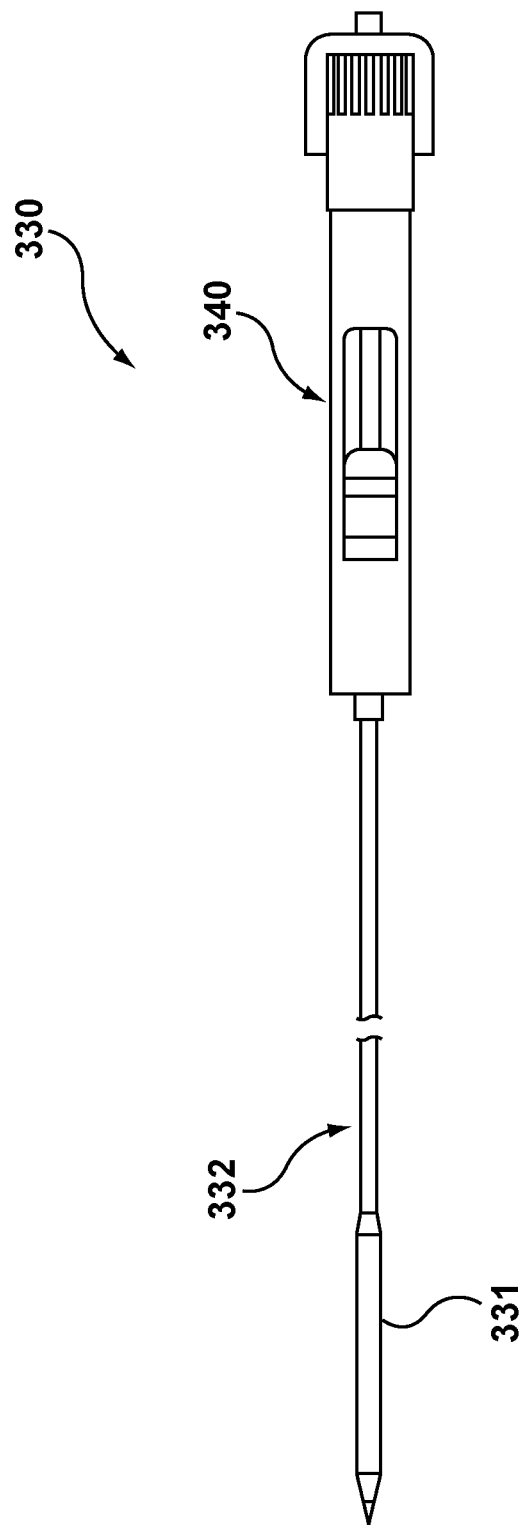
FIG. 3 is a catheter-based heart valve prosthesis delivery device in accordance with an embodiment hereof.
Figure 3A:
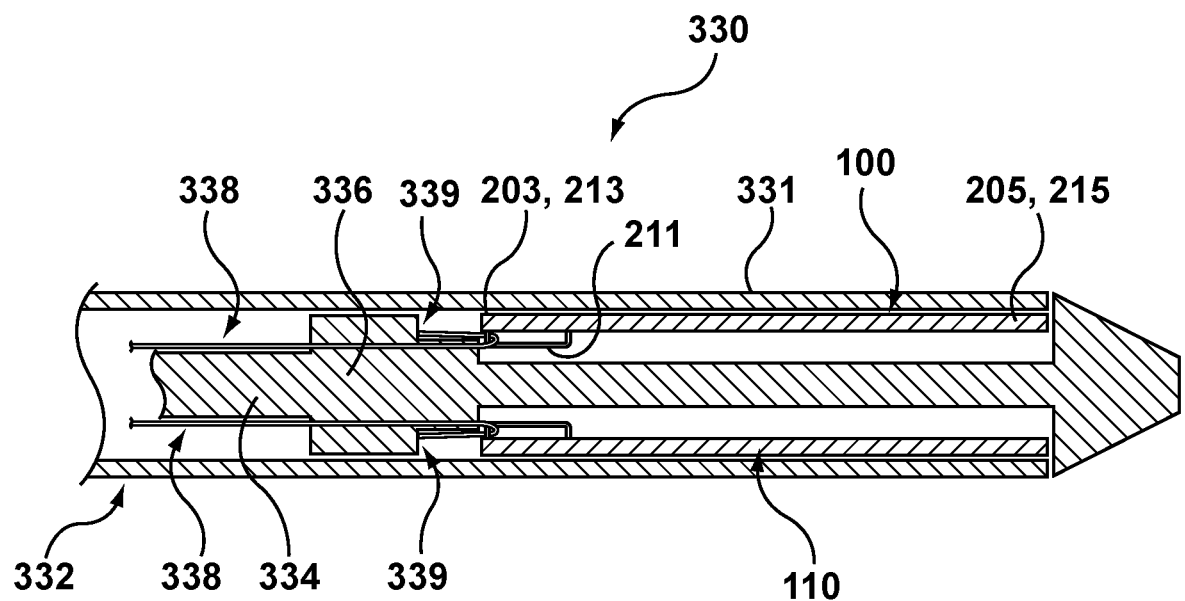
FIGS. 3A-3E depict sectional views of a distal portion of the delivery device of FIG. 3 with a heart valve prosthesis of FIG. 1 shown compressed in an initial delivery configuration in FIG. 3A and shown in various stages of deployment therefrom in FIGS. 3B-3E.

In general terms and with reference to FIGS. 3 and 3A-3E, prosthesis 100 is coupled to inner shaft assembly 334 via hub assembly 336 and compressively retained in a delivery state within a capsule 331 of delivery sheath assembly 332. In embodiments hereof, hub assembly 336 may include or provide one or both of a valve support and a valve retainer as described in the '242 application. A plurality of tethers or elongate members 338 connect inflow end 213 of heart valve prosthesis 100 to a remainder of delivery device 330, for example to hub assembly 336. In embodiments hereof, tensioning of the plurality of tethers aids in collapsing heart valve prosthesis 100 during loading of the prosthesis into a delivery state within capsule 331 of delivery device 330, as shown in FIG. 3A. Through operation of handle assembly 340, delivery sheath assembly 332 may be manipulated to proximally withdraw capsule 331 from covering or enclosing heart valve prosthesis 100 to thereby permit the prosthesis to self-expand from a compressed, delivery state into a partial deployment state and thereafter into a full deployment state. In the partial deployment state, heart valve prosthesis 100 is still attached to delivery device 330 by tethers 338 that maintain a connection between the prosthesis and the delivery device 330. Imaging by fluoroscopy or other imaging technology may be performed while heart valve prosthesis 100 is in the partial deployment state in order to ascertain a position of the heart valve prosthesis at the target implantation site. If the step of imaging shows heart valve prosthesis 100 to be improperly or sub-optimally positioned at the target implantation site, tensioning of tethers 338 may adjusted or maintained to permit recapture or repositioning of the heart valve prosthesis. For instance, tethers 338 may be subjected to increased tension while still attached to inflow end 213 of heart valve prosthesis 100 to thereby cause the inflow portion 202 of frame 110 to at least partially re-collapse or compress for repositioning or for recapturing of the prosthesis. In an embodiment, heart valve prosthesis 100 may be recaptured within a separate recapture sheath (not shown) that may be advanced over delivery sheath assembly 332.

As noted above, tethers 338 connect inflow end 213 of heart valve prosthesis 100 with hub assembly 336. The tensioning of tethers 338 may be manipulated to permit controlled release of inflow portion 202 of frame 110 and thereby provide expansion of the inflow area of heart valve prosthesis 100 during deployment from delivery device 330 at a slower or reduced rate, such that expansion of at least that portion or end of the prosthesis may be controlled. In order to permit full deployment of the prosthesis, tension is removed from the plurality of tethers 338 to thereby permit heart valve prosthesis 100 to fully expand into apposition with the heart and to achieve a final full deployment state.

FIG. 3A is a sectional view of a distal portion of delivery device 330 with heart valve prosthesis 100 held in a compressed, delivery state within capsule 331, as described above. In order to simplify the sectional depictions of the delivery system shown in FIGS. 3A-3E, support arms 206A, 206B and other detail of heart valve prosthesis 100 are not shown. Heart valve prosthesis 100 is shown oriented within capsule 331 such that inflow end 203 of frame 110 is proximal of outflow end 205 of frame 110, or stated another way such that inflow end 215 of the prosthesis is proximal of outflow end 215 of the prosthesis. Consequently when loaded within delivery device 330, inflow or upstream end 213 of heart valve prosthesis 100 may be viewed as being a proximal end of the prosthesis and outflow or downstream end 215 of heart valve prosthesis 100 may be viewed as being a distal end of the prosthesis. In other embodiments, an orientation of heart valve prosthesis 100 can be reversed relative to the delivery device. One or more tethers 338 are connected to corresponding anchor guides or rails 211 of the prosthesis. For example, in the view of FIG. 3A, two tethers 338 are provided with each tether being connected to a respective rail 211. In other embodiments, a single tether 338 or more than two tethers 338 may be utilized. Each of the tethers 338 defines a leading end 339 opposite a trailing end (not shown), such that a respective tether 338 is looped through rail 211 of frame 110. In the embodiment shown in FIGS. 3A-3E, leading ends 339 of tethers 338 are operatively connected to hub assembly 336 with the trailing end of each tether 339 being operatively coupled to handle assembly 340.

In accordance with embodiments hereof, delivery device 330 may be used to deliver heart valve prosthesis 100 to the target site of a native heart valve via a transatrial or transseptal implantation procedure. Generally in a transseptal implantation procedure for replacing a native mitral valve, a prosthetic valve delivery system is introduced into the vasculature via a percutaneous entry point, a.k.a the Seldinger technique, and then tracked through the vasculature and eventually into the left atrium so that a distal tip of the delivery system may be positioned proximate the native mitral valve. More particularly in an embodiment hereof, the percutaneous entry point may be formed in a femoral vein via the Seldinger technique. Thereafter, a guidewire (not shown) may be advanced through the vasculature to eventually arrive at the heart. The guidewire may be then directed into and through the right atrium and thereafter into the left atrium after it gains access thereto either by puncturing the atrial septum with the aid of a transseptal needle or by being passed through a pre-existing hole therein. Once the guidewire is positioned, the endoluminal entry port and the access ports through the atrial septum are dilated to permit entry of a guide catheter (not shown) and/or delivery device 330 into the left atrium. Thereafter, delivery device 330 may be advanced into the left atrium through the punctured atrial septum and positioned proximate to the native mitral valve. Although not shown, it will be understood by those of ordinary skill in the art that a prosthetic valve delivery system, such as delivery device 330, may be inserted into a guide catheter in order to be advanced to a position proximate to the native mitral valve. Suitable transatrial and/or transseptal implantation procedures that may be adapted for use with heart valve prosthesis described herein are disclosed in U.S. Appl. Pub. No. 20140046433 to Igor Kovalsky and U.S. Appl. Pub. No. 2012/0035722 to Tuval et al, each of which is incorporated by reference herein in its entirety.

Figure 3B:
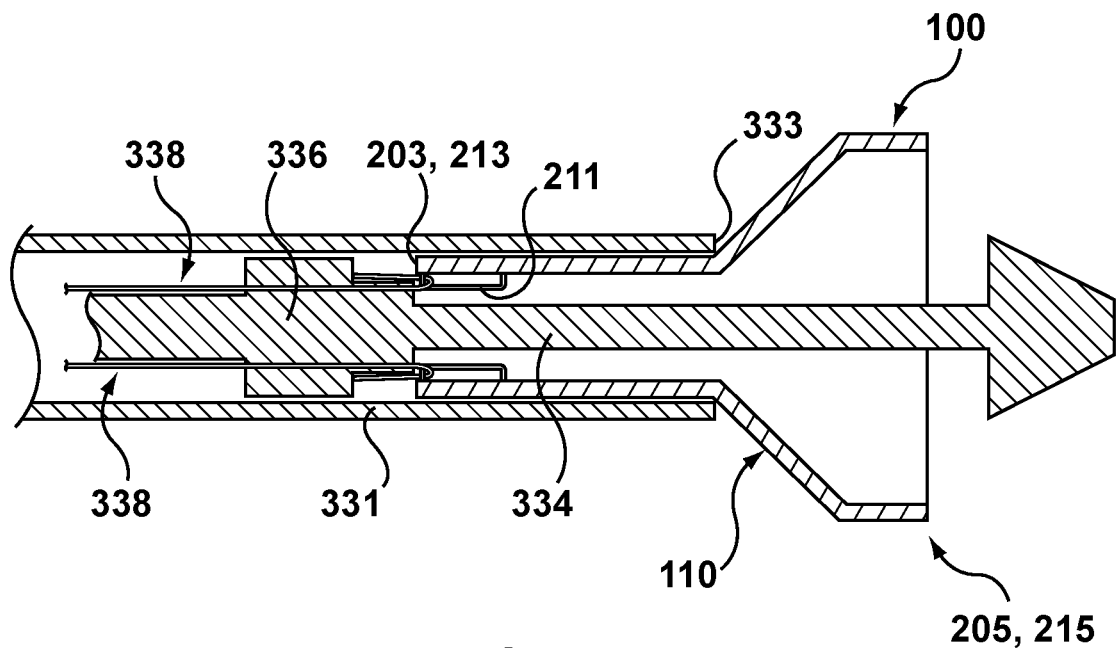

Following transatrial or transseptal delivery of compressed heart valve prosthesis 100 to the native mitral valve via delivery device 330, delivery device 330 is operated to deploy the heart valve prosthesis by proximally retracting capsule 331. FIG. 3B illustrates a partial release of heart valve prosthesis 100 from delivery device 330 in which capsule 331 is partially retracted from covering the prosthesis with a proximal segment of heart valve prosthesis 100 still being held compressed within capsule 331. The now-exposed distal segment of heart valve prosthesis 100 that extends distal of capsule 331 is permitted to self-expand upon release to or toward the normal or expanded configuration thereof. Since the proximal segment of heart valve prosthesis 100 remains in the compressed condition within the confines of capsule 331, the prosthesis is still captured or robustly connected to delivery device 330. Further, tethers 338 remain connected to rails 211 and are maintained in essentially their delivery configuration in FIG. 3B.

Figure 3C:
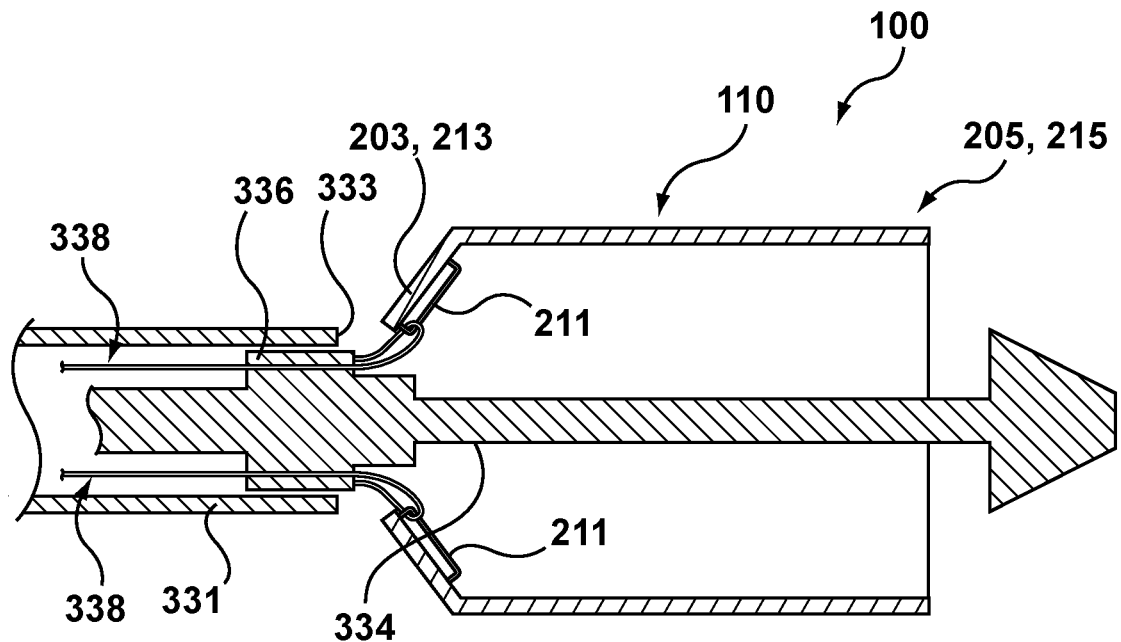

Upon continued proximal retraction of capsule 331, a partial deployment state of the heart valve prosthesis is reached, as shown in FIG. 3C. A distal end 333 of capsule 331 is now proximal of the upstream end 213 of the prosthesis, with tethers 338 held in tension to maintain the connection between rails 211 of the prosthesis and delivery device 330. The tethers 338 may be held in tension, for e.g., by having the trailing end (not shown) of each of the tethers 338 coupled to corresponding actuatable or manipulate-able mechanism(s) provided in handle assembly 340 that allow a user to control tension in the tethers. The tensioned tethers 338 serve to control expansion of inflow portion 202 of self-expanding frame 110, and accordingly control deployment of the proximal or upstream end 213 of prosthesis 100. The tensioned tethers 338 prevent uncontrolled and/or undesirable rapid self-expansion from occurring. Instead, tension in the tethers 338 may have a controlled released to thereby allow inflow portion 202/upstream end 213 to transition toward the normal, expanded configuration of frame 110/prosthesis 100 in a controlled, more predictable manner, as generally reflected in FIGS. 3C-3E.

Figure 3D:
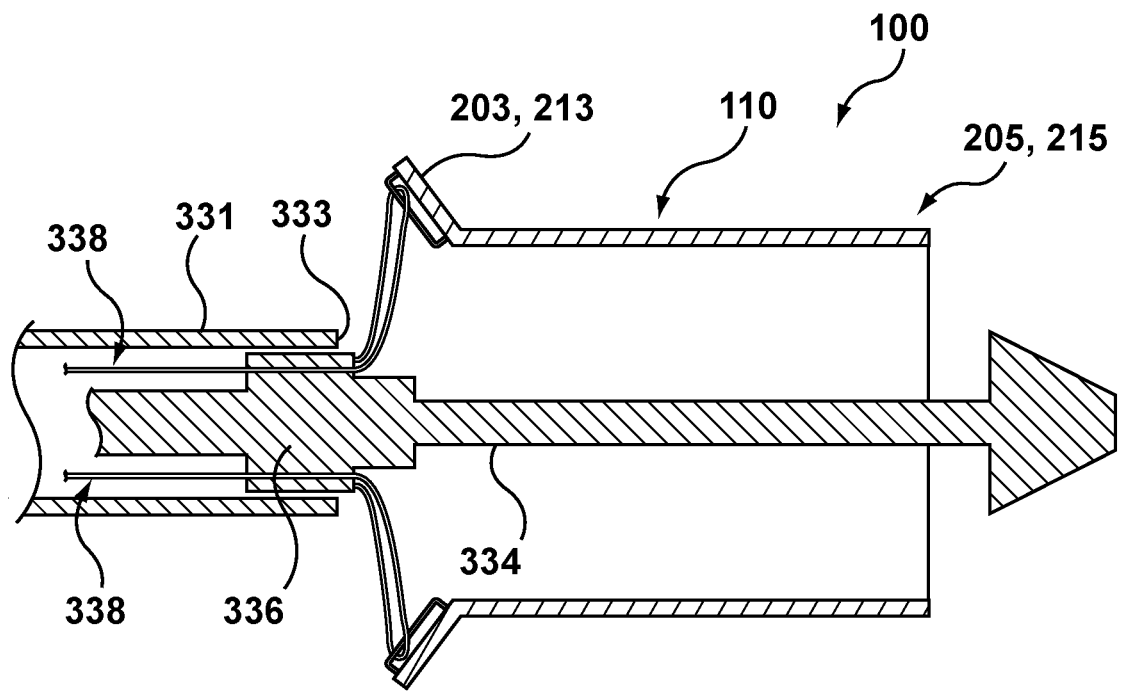
Figure 3E:
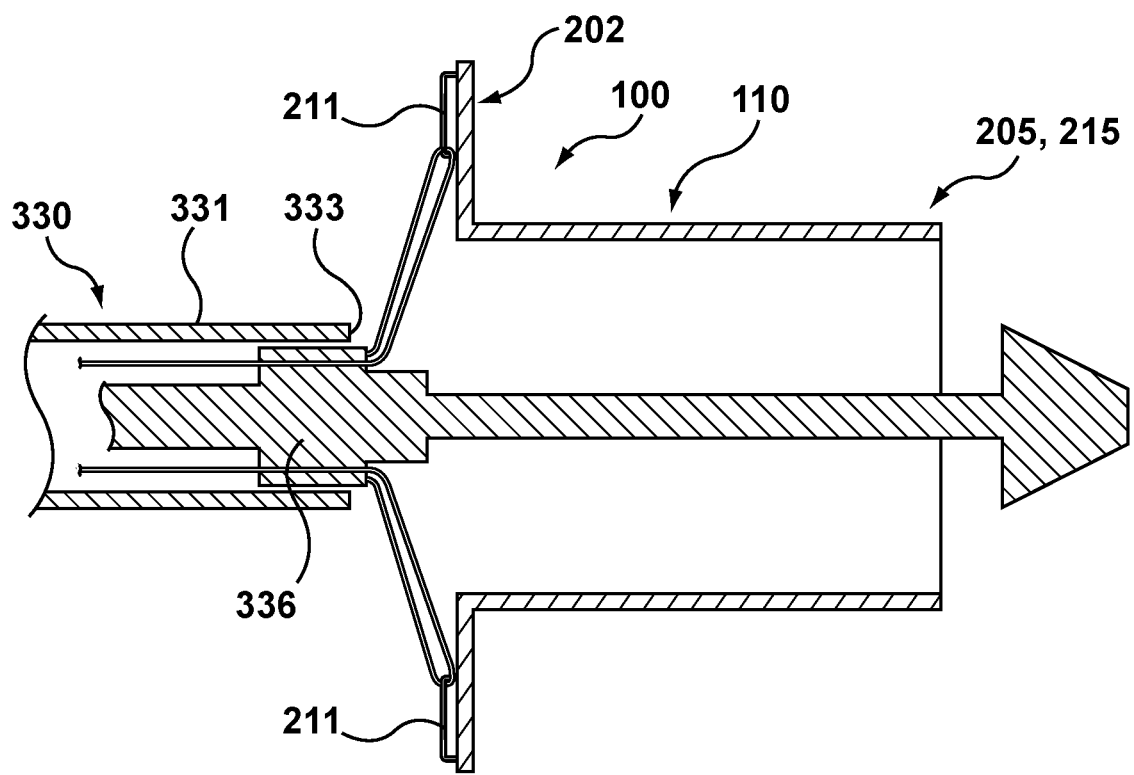

With tensioning of tethers 338 being released or reduced, inflow end 213 of heart valve prosthesis 100 is permitted to further expand as represented by another partial deployment state of FIG. 3D. In embodiments hereof heart valve prosthesis 100 may be held in a partial deployment state for imaging, such as in either of the partial deployment states shown in FIGS. 3C and 3D. If imaging of the partially deployed heart valve prosthesis evidences a poor implantation result, tethers 338 may be then manipulated to perform a recapture procedure. For example, tension in tethers 338 may be increased to cause inflow portion 203/upstream end 213 of prosthesis 100 to re-collapse or compress and thereby transition from the partially expanded configuration of FIG. 3C or 3D, for example, to or toward the compressed, delivery state of FIG. 3A or 3B. Once inflow portion 203/upstream end 213 is re-collapsed, an entirety of heart valve prosthesis 100 may more easily be compressed for repositioning and/or recapture. In an embodiment, a separate recapture sheath (not shown) may be slidably advanced over capsule 331 and the compressed or partially compressed heart valve prosthesis 100 to effectuate recapture.

Figure 4:
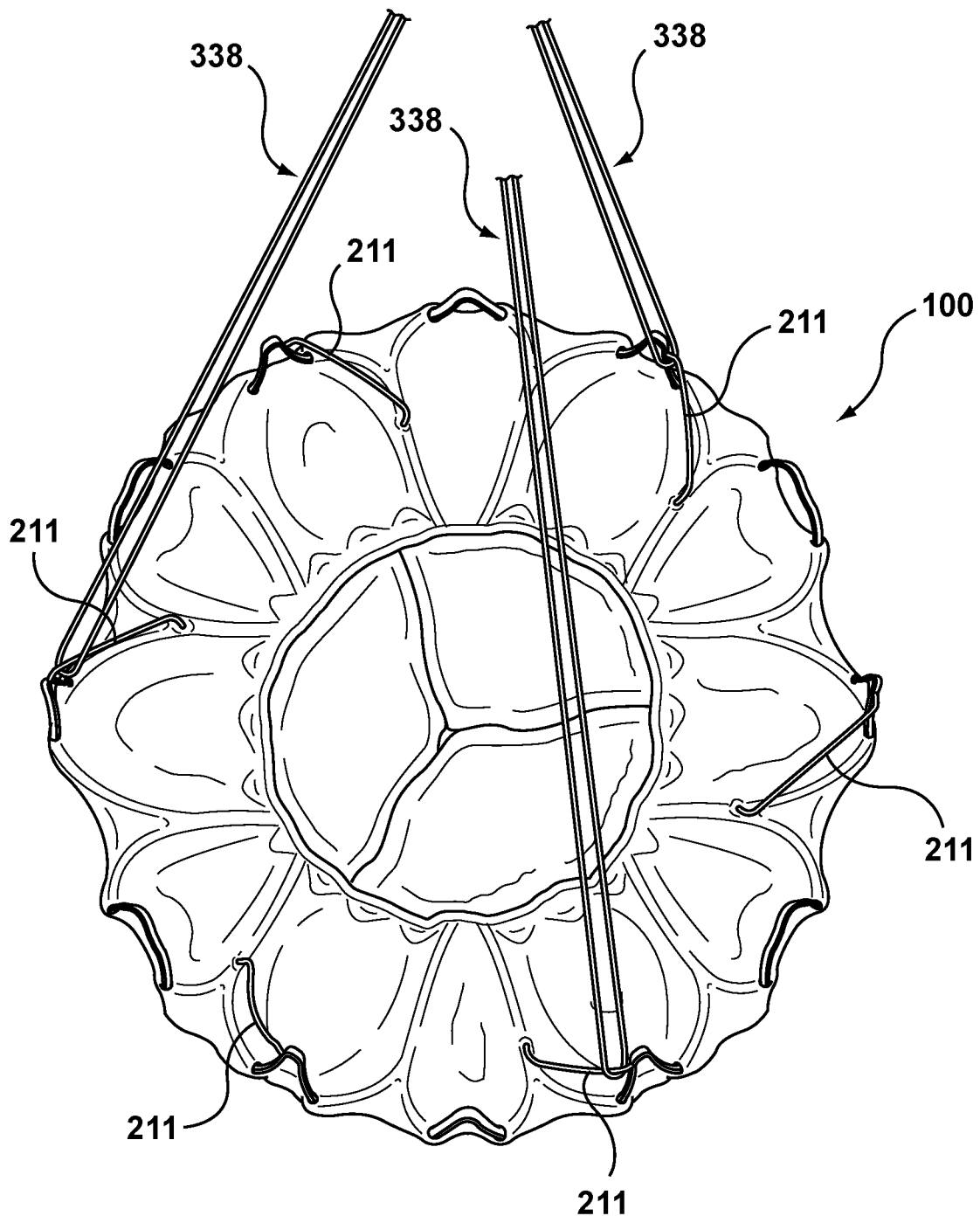
FIG. 4 is a perspective view of an inflow area of the heart valve prosthesis of FIG. 1 after implantation with a plurality of elongate guide members proximally extending therefrom.

Once tension in tethers 338 has been sufficiently lessened to permit upstream end 213 of heart valve prosthesis 100 to self-expand to its deployed configuration and after a suitable deployment or implantation of the prosthesis has been confirmed, delivery device 330 may be proximally retracted while tethers 338 are permitted to remain looped through rails 211 of heart valve prosthesis 100. Thereafter the trailing and leading ends of tethers 338 may be decoupled from delivery device 330 such that tethers 338 remain proximally extending from rails 211 of heart valve prosthesis 100 after full deployment or implantation, as shown in FIG. 4.

Figure 5:
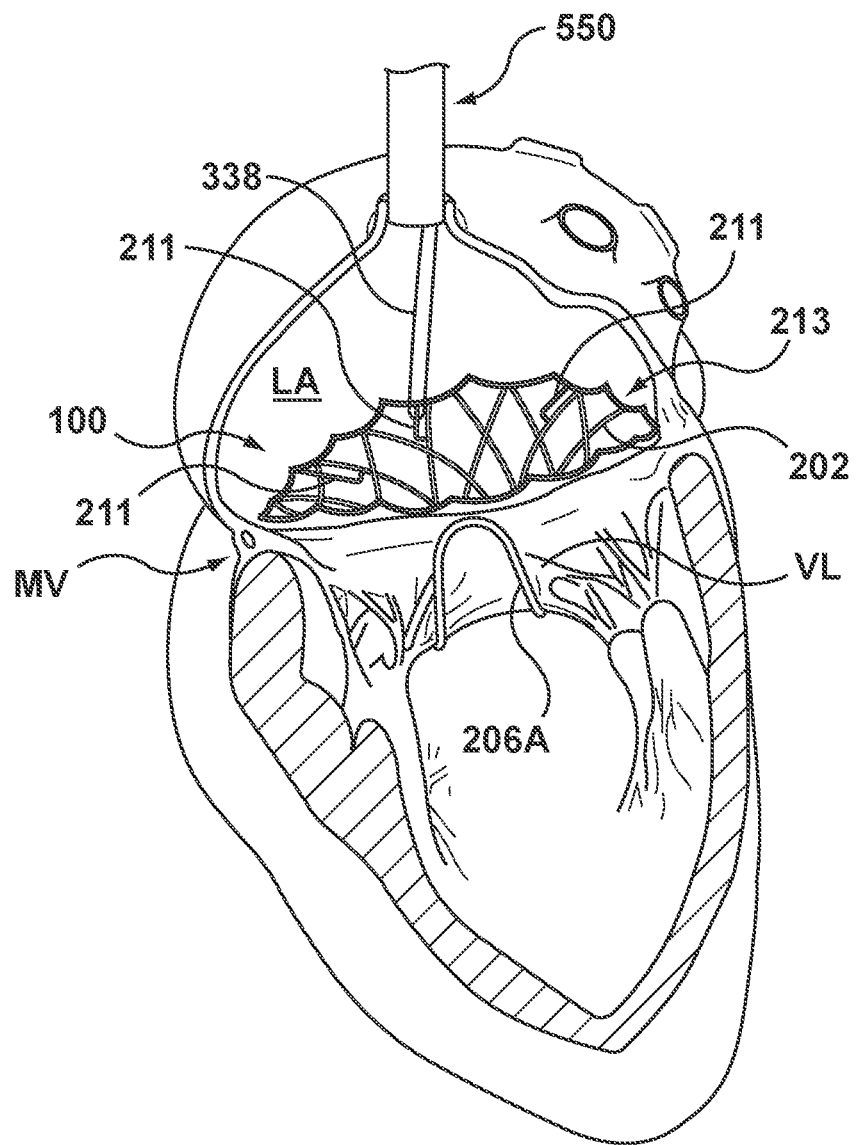
FIG. 5 depicts the heart valve prosthesis as shown in FIG. 4 implanted within a heart to replace a native mitral valve.

FIG. 5 depicts heart valve prosthesis 100 after having been deployed or implanted within a native mitral valve MV via a transseptal or transapical procedure. Upstream end 213 of heart valve prosthesis 100 is shown sitting against and/or conforming to a floor of the left atrium LA with support arm 206A of heart valve prosthesis 100 shown capturing a native valve leaflet VL. In order to simplify the depiction in FIG. 5, only a single tether or elongate guide member 338 is shown proximally extending from its corresponding rail 211, but it should be understood that more than one tether or elongate guide member may be used, such as the three tethers or elongate guide members shown in FIG. 4. The proximally extending tether 338 may now be used as elongate guide member to guide an anchor tool to its respective rail 211 of implanted heart valve 100 as described below. Accordingly from here onward in the description, tethers 338 will be referred to as elongate guide members 338.

Elongate guide member 338 is shown in FIG. 5 as proximally extending from rail 211 into a guide catheter 550 with each of its leading and trailing ends (not shown) extending externally of a patient for access and use by a clinician. In order to provide additional anchoring to heart valve prosthesis 100, elongate guide member 338 is used to guide an anchor tool to rail 211 such that the anchor tool may be used to deploy an anchor clip through upstream end 213 of heart valve prosthesis 100 and into tissue of the left atrium.

A suitable anchor tool 660 and anchor clip 662 for use in an embodiment hereof are shown in FIGS. 6 and 6A-6C. For use in embodiments hereof, anchor clip 662 may be constructed from a single Nitinol wire and formed to have a shape memory to return to the state shown in FIG. 6C upon release from anchor tool 660. Anchor tool 660 has a distal portion that is flexible enough to be tracked to a target site and includes an elongate outer tube 664 with a pusher rod 666 that slidable extends therein. Outer tube 664 has a distal end 663 within which is disposed an anchor clip holder 668, which is shown in various stages of operation in FIGS. 6A-6C. Anchor clip holder 668 includes a spaced pair of anchor clip guides 665A, 665B between which a distal end of pusher rod 666 is slidably disposed. The distal end of pusher rod 666 includes a laterally-extending groove 661 formed therein that aligns with opposing longitudinally-extending slots 667A, 667B of anchor clip guides 665A, 665B.

FIG. 6A depicts pusher rod 666 in an initial, retracted delivery position with anchor clip 662 loaded therein in a straightened delivery state. Straightened anchor clip 662S has a U-shape and is loaded within anchor clip holder 668 such that a connector portion 662c is receiving with groove 661 of pusher rod 666 and hook portions 662a, 662b are held in a straightened state within respective anchor clip guides 667A, 667B. FIG. 6B depicts pusher rod 666 being distally translated to deploy anchor clip 662, which is shown in a partially deployed state with hook portions 662a, 662b beginning to resume their looped or coiled shape. When anchor tool 660 and anchor clip 662 are used in a method of anchoring upstream end 213 of heart valve prosthesis 100 within a left atrium of the heart, hook portions 662a, 662b of anchor clip 662 will resume their looped or coiled shape while passing through each of upstream end 213 and corresponding tissue of the left atrium. FIG. 6C depicts pusher rod 666 after having been fully distally translated such that anchor clip 662 is released from anchor tool 660 and fully resumes its looped or coiled shaped. Suitable anchor tools and clips that may be adapted for use in methods described herein are disclosed in U.S. Pat. No. 6,945,980 to Nguyen et al., U.S. Appl. Pub. No. 2001/0018592 to Schaller et al. and U.S. Appl. Pub. No. 2009/0264903 to Lee et al., each of which is incorporated by reference herein in its entirety.

Figure 7:
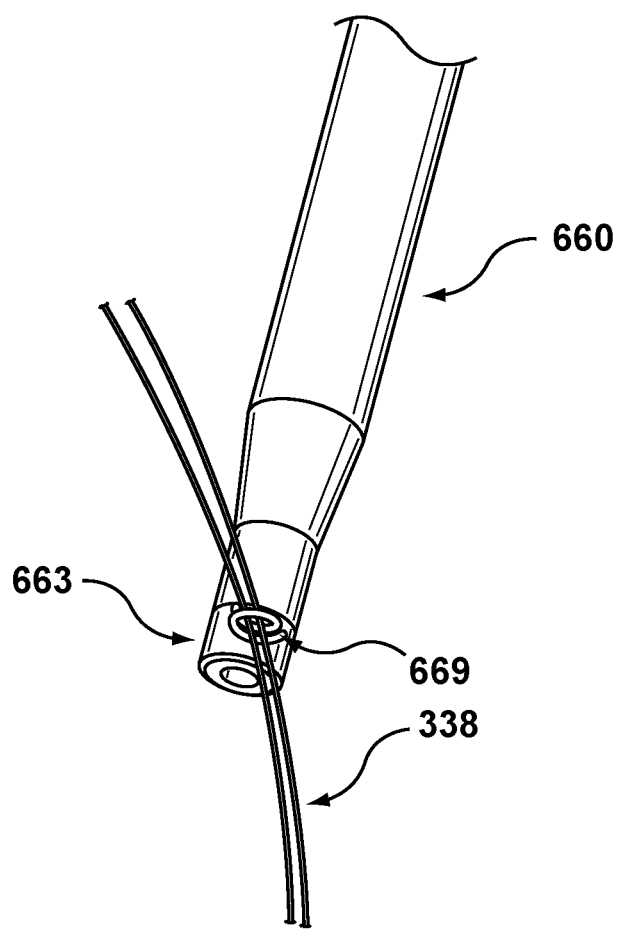
FIG. 7 is a perspective view of a distal end of the anchor tool of FIG. 6 attached to an elongate guide member in accordance with an embodiment hereof.

FIG. 7 is an enlarged perspective view of distal end 663 of anchor tool 660. An elongate guide member 338 is slidably received within a coupling eyelet 669 that is attached to distal end 663 of anchor tool 660. Coupling eyelet 669 is configured to permit elongate guide member 338 to be transversely introduced or received within an interior of the coupling eyelet. In embodiments hereof, when a clinician attaches anchor tool 660 to a respective elongate guide member, either a single proximally-extending segment or both proximally-extending segments of the elongate guide member may be slidably received within coupling eyelet 669.

Figure 8A:
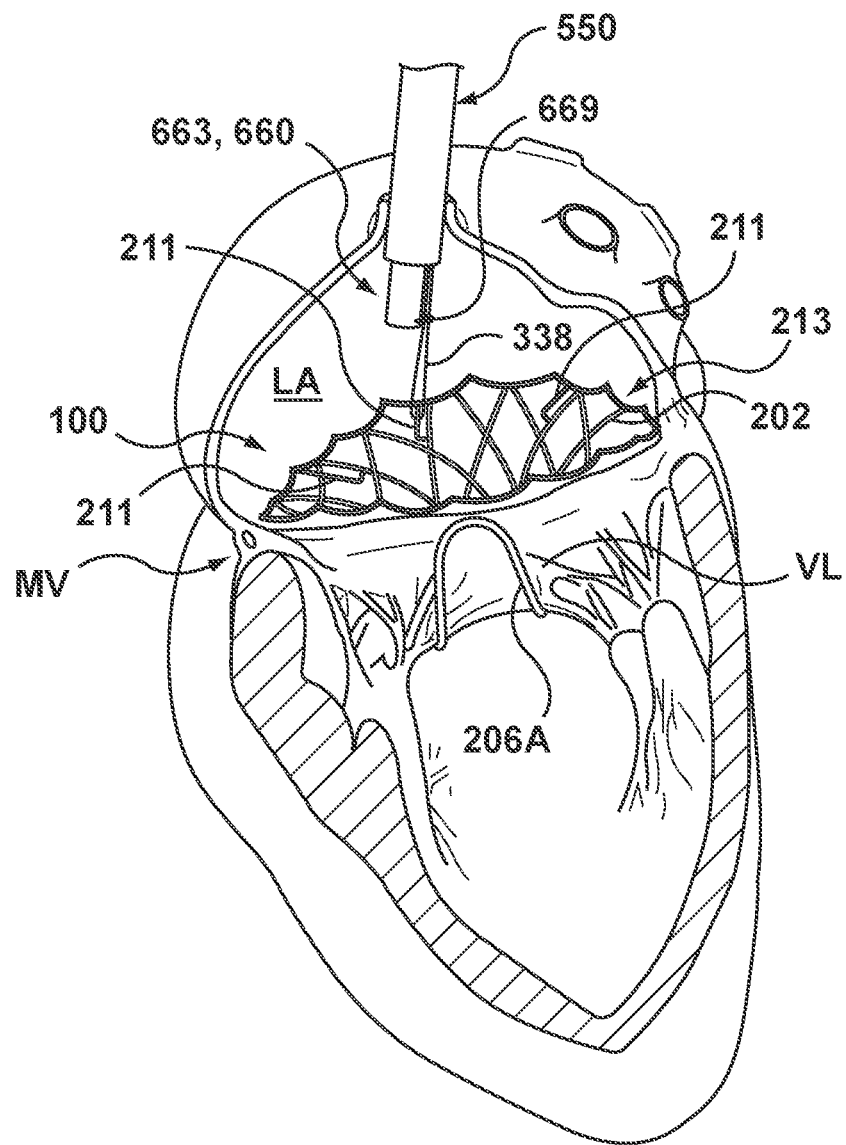
FIGS. 8A-8C illustrate a method of securing or anchoring a heart valve prosthesis within a native mitral valve of a patient in accordance with an embodiment hereof.
Figure 8B:
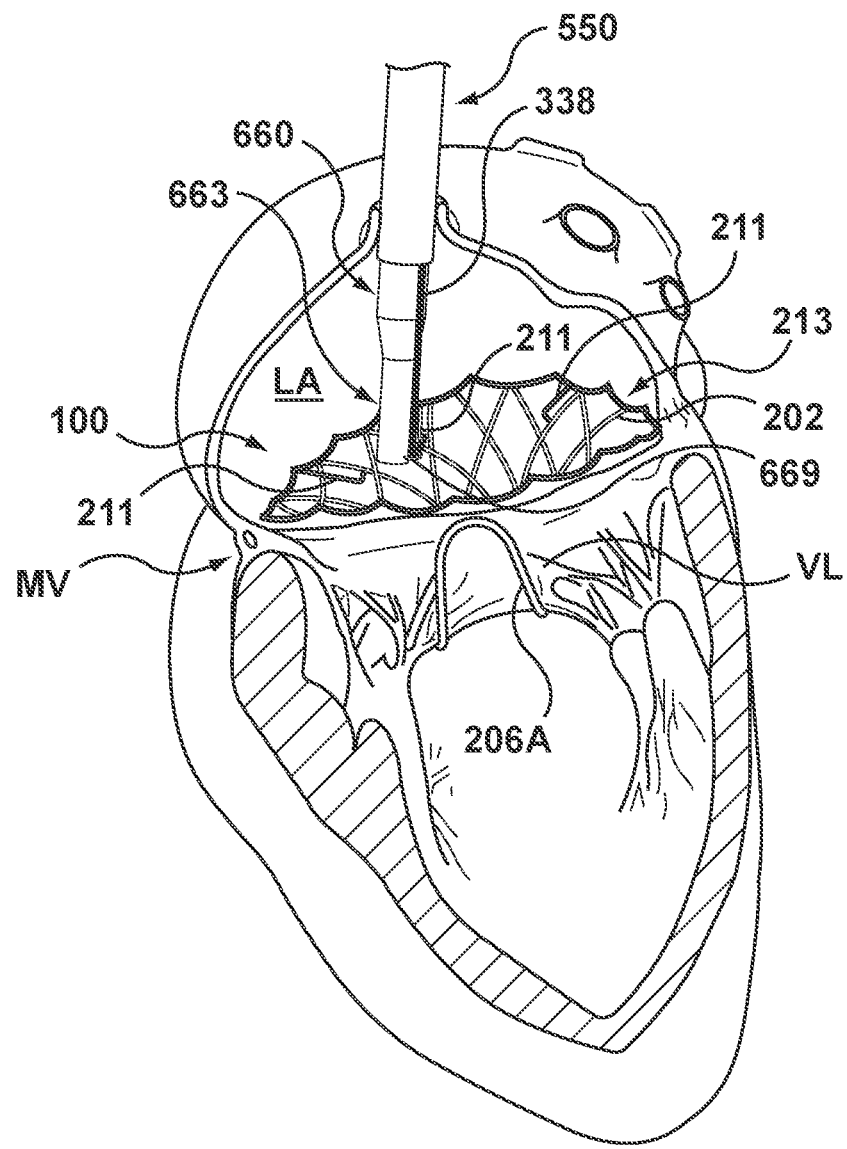
Figure 8C:
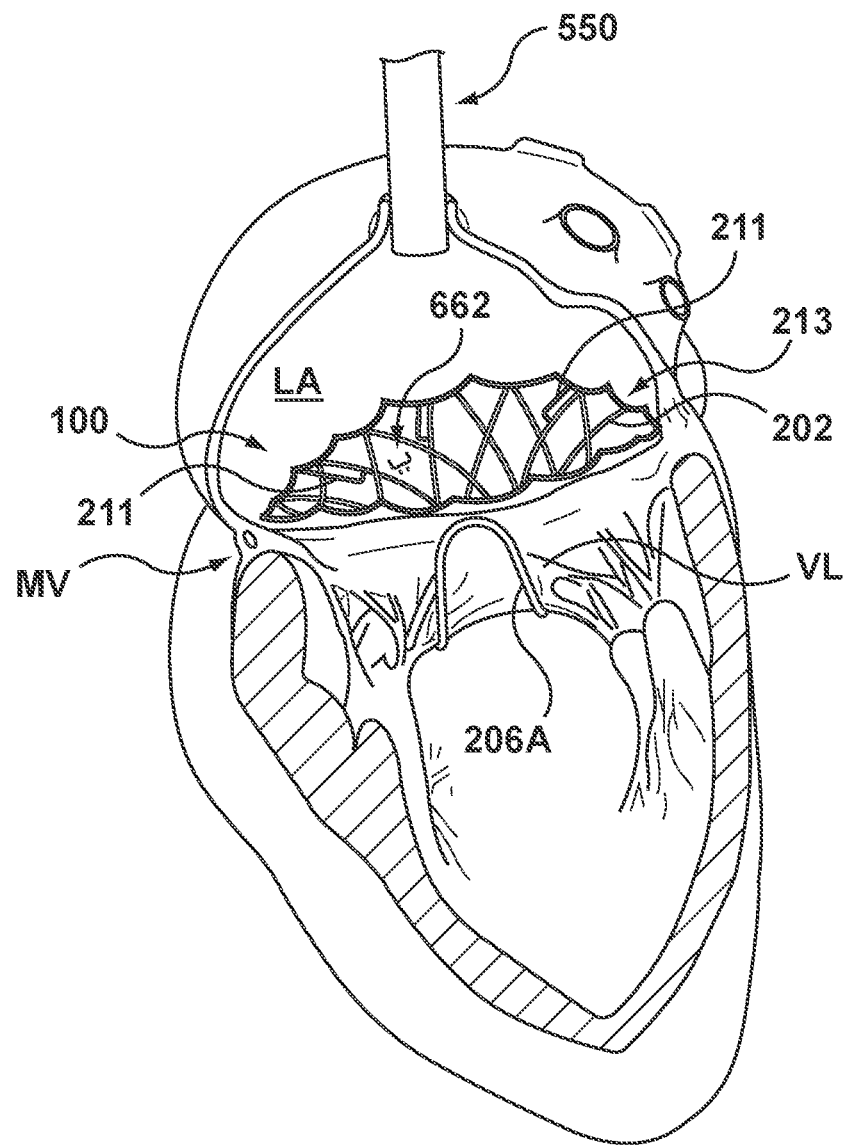

FIGS. 8A-8C illustrate a method of securing or anchoring heart valve prosthesis 100 to a heart of a patient with anchor clip 662. In embodiments in accordance herewith, securing an inflow or upstream area of a heart valve prosthesis with one or more anchor clips in accordance herewith prevents movement of a frame of the heart valve prosthesis which may in turn prevent the frame from failing over time due to fatigue. As well preventing movement of the heart valve prosthesis by using one or more anchor clips in accordance herewith may also prevent paravalvular leakage from developing after implantation. In other embodiments in accordance herewith, a securement site for an anchor clip may be determined by checking for leakage after the heart valve prosthesis is initially implanted or deployed. For instance, color Doppler imaging may be used to check for paravalvular leakage after the heart valve prosthesis is initially fully deployed into apposition with the heart, and if leakage is identified, than an anchor clip may be advanced to a securement site in the area of leakage, in accordance with the method described below, such that the anchor clip may then be secured to the prosthesis and the tissue of the heart at the securement site to thereby provide a better seal therebetween and to prevent further paravalvular leakage.

FIGS. 8A-8C are steps performed after heart valve prosthesis 100 has been implanted within the native mitral valve MV, as shown and described with reference to FIG. 5, and with anchor tool 660 attached to the leading and trailing ends of elongate guide member 338. As described above, anchor tool 660 is slidably attached to elongate guide member 338 via coupling eyelet 669. Anchor tool 660 is introduced within a proximal end (not shown) of guide catheter 550 and advanced along elongate guide member 338 until distal end 663 of anchor tool 660 is positioned adjacent to rail 211 of heart valve prosthesis 100, as shown in FIG. 8A. Anchor tool 660 is further advanced along elongate guide member 338 until a desired securement site on upstream end 213 of heart valve prosthesis 100 is reached, as shown in FIG. 8B. It should be understood by one of ordinary skill in the art that due to the sliding interaction between elongate guide member 338 and rail 211, a clinician will have some maneuverability as to where anchor tool distal end 663 may be positioned with respect to rail 211, and thus will have some flexibility as to where anchor clip 662 will be secured through the heart valve prosthesis relative to rail 211. In embodiments hereof, distal end 663 of anchor tool 660 may be positioned to either side of rail 211 along a length thereof and/or may be positioned proximal or distal of an end 212a, 212b of rail 211. FIG. 8C depicts anchor clip 662 fully deployed or released from anchor tool 660, with anchor tool 660 and elongate guide member 338 proximally retracted and removed from the patient. Upon release from anchor tool 660, as previously discussed above, hook portions 662a, 662b of anchor clip 662 will resume their looped or coiled shape while passing through each of upstream end 213 and corresponding tissue of the left atrium to secure the heart valve prosthesis 100 thereto. The steps of deploying an anchor clip 662 at a respective securement site of the heart valve prosthesis may be repeated, as desired, by moving the elongate guide member along the rail to the next site. Once all anchor clips for deployment proximate to the rail have been deployed, the elongate guide member may be pulled free of the rail and removed. Thereafter the steps of deploying an anchor clip 662 at a respective securement site of the heart valve prosthesis may be repeated for one or more elongate guide members 338 that remain proximally extending therefrom.

Figure 9A:
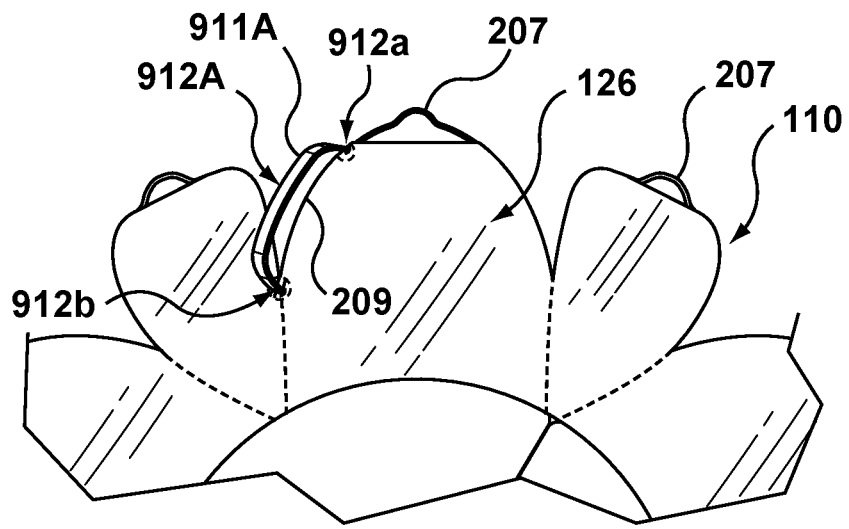
FIGS. 9A and 9B depict anchor guides in accordance with alternate embodiments hereof.
Figure 9B:
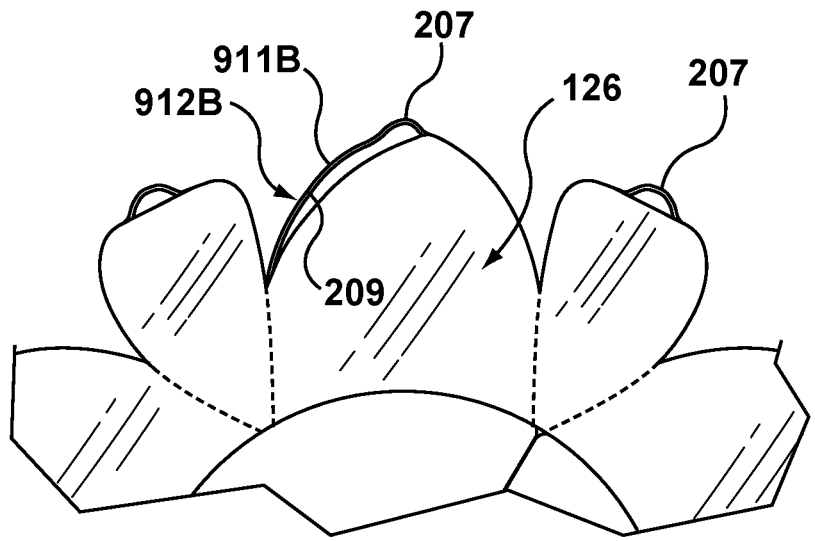

Each of FIGS. 9A and 9B is an enlarged view of a portion of an inflow area of FIG. 1A in accordance with another embodiment hereof, and depict anchor guides 912A, 912B, respectively. Anchor guide 912A is a rail 911A formed from a biocompatible fabric and, similar to rail 211 described above, may extend substantially parallel to a corresponding strut 209 of frame 110 with a first end 912a being disposed adjacent to a crown 207 of frame 110 and a second end 912b being disposed along strut 209. Fabric rail 911A is formed similar to a belt loop with first end 912a being attached to graft material 126 adjacent to crown 207 and second end 912b being attached to graft material 126 at a point along underlying strut 209 that is spaced from crown 207. In accordance with embodiments hereof, fabric rail 911A may be attached to graft material 126, for example, by using a suitable adhesive or by being sewn thereto. In another embodiment, fabric rail 911A may be attached to both graft material 126 and underlying structure of frame 110, such as strut 209, by being sewn thereto. Anchor guide 912B of FIG. 9B is a rail 911B that is a segment of strut 209 where graft material 126 is left unsewn or unattached to the strut. Each of rails 911A, 911B that forms a respective anchor guide 912A, 912B functions similar to rail 211 of anchor guide 212 and permits tether or elongate guide member 338 to be used to aid in loading a heart valve prosthesis, to control expansion of a heart valve prosthesis, to be used to recapture a heart valve prosthesis when necessary, and/or to be slidably coupled thereon for directing an anchor tool to a securement site as described above.

Various features of delivery device 330 as shown and described with reference to FIGS. 3 and 3A-3E above can be modified or replaced with differing structures and/or mechanisms. Thus, apparatus and methods in accordance with embodiments hereof are not limited to the delivery sheath assembly 332, the inner shaft assembly 334, the hub assembly 336 or the handle assembly 340 as shown. Any construction of a delivery system that generally facilitates compressed loading of a self-expanding heart valve prosthesis over an inner shaft via a retractable outer sheath or capsule is acceptable as long as one or more tethers may be employed therewith to perform one or more functions as described herein for embodiments hereof.

Figure 10A:
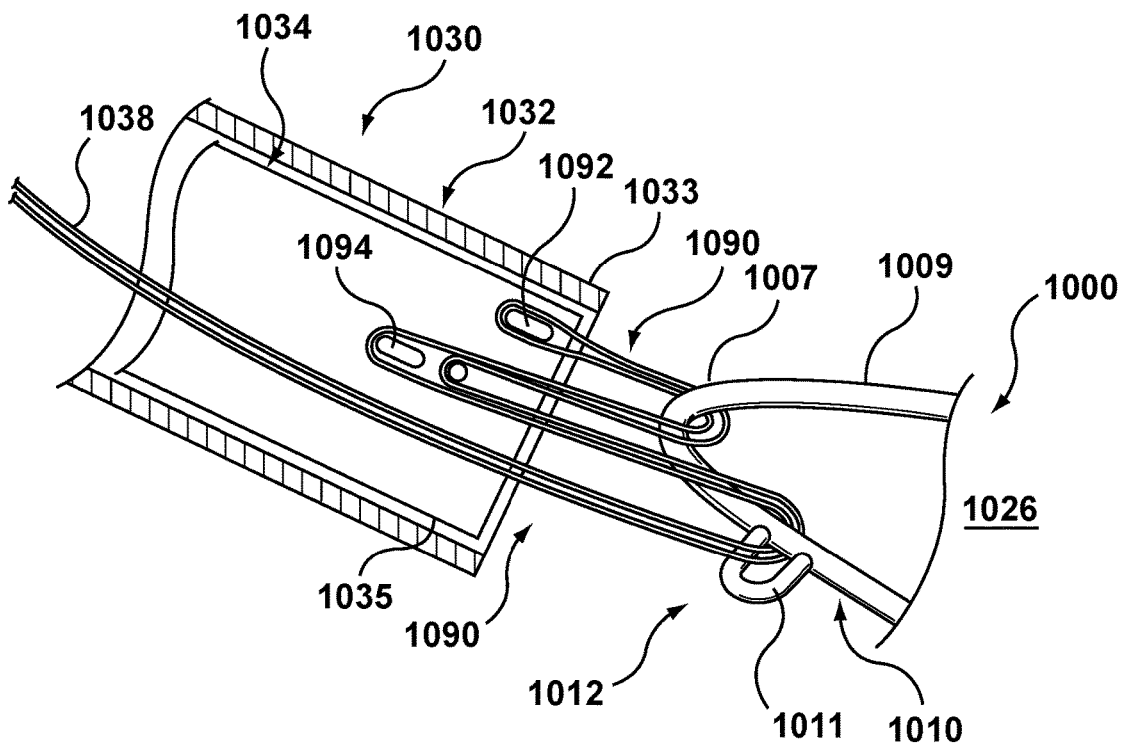
FIGS. 10A-10D illustrate a method of deploying and securing or anchoring a heart valve prosthesis within a heart of a patient in accordance with another embodiment hereof.
Figure 10B:
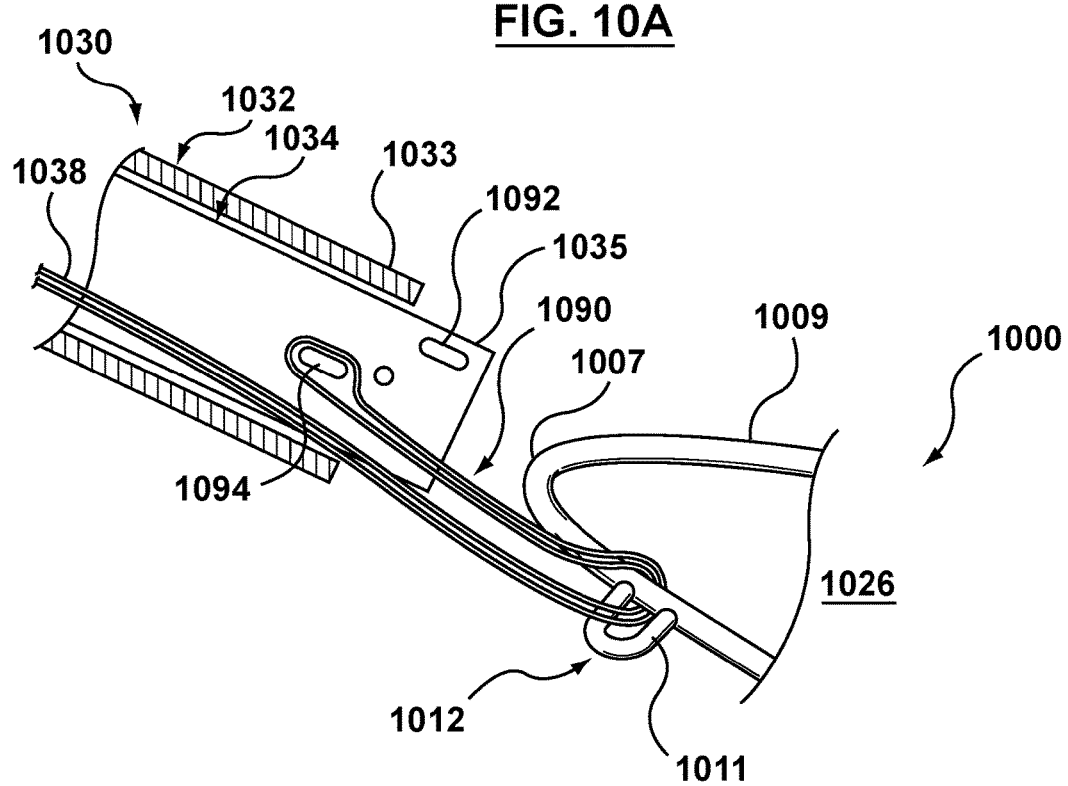

For example, a portion of another embodiment of a delivery system and a prosthetic heart valve in accordance herewith is shown in FIGS. 10A-10D. FIGS. 10A and 10B depict a sectional view of a distal portion of a delivery device 1030 with a heart valve prosthesis 1000 deployed from a distal end 1033 of a delivery sheath assembly 1032. In each of FIGS. 10A and 10B, heart valve prosthesis 1000 is in a partial deployment state such that it remains attached to delivery device 1030 by one or more tethers or elongate members 1038 as described in more detail below. A single crown 1007 and anchor guide 1012 of heart valve prosthesis 1000 are shown in FIGS. 10A and 10B so that a connection between the respective tether or elongate guide member 1038, crown 1007, anchor guide 1012 and an inner shaft assembly 1034 may be more clearly depicted. It would be understood by one of ordinary skill in the art that heart valve prosthesis 1000 would be attached by more than the connection shown in FIG. 10A, and that one or more additional connections may be made between the inner shaft assembly 1034 of delivery device 1030 and respective crown 1007 and anchor guide 1012 of the heart valve prosthesis by one or more additional tethers or elongate guide members 1038.

Figure 10C:
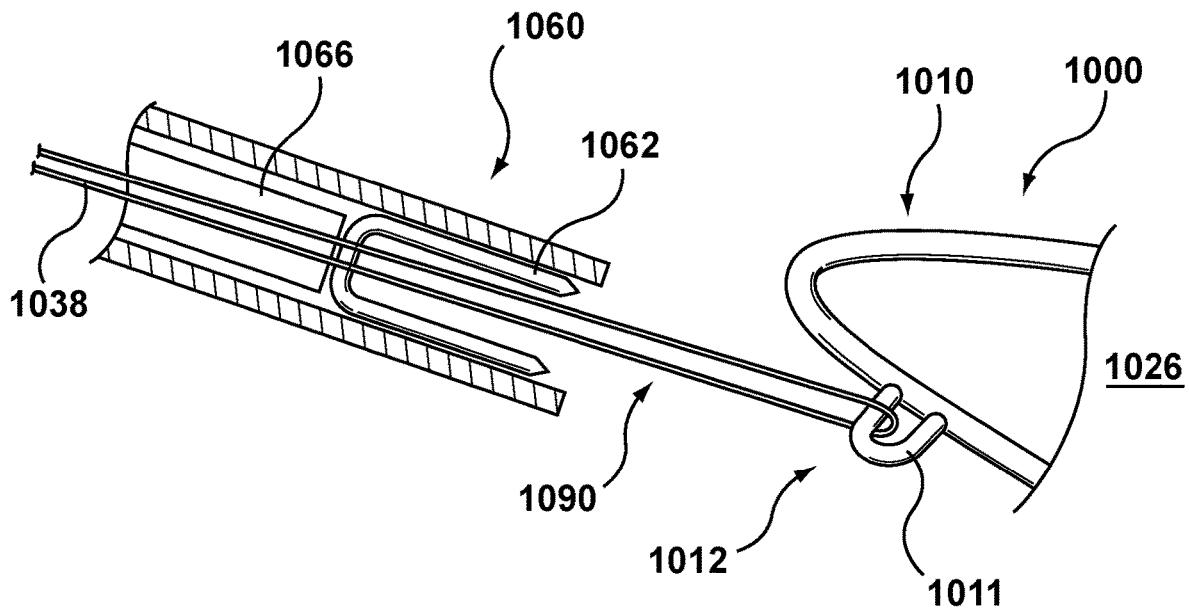

In the heart valve prosthesis embodiment shown in FIGS. 10A-10D, anchor guide 1012 is an anchor guide eyelet 1011 that extends from a strut 1009 of frame 1010 at a location that is spaced from crown 1007 and that is not covered by a graft material 1026. Tether 1038 has a looped end 1090 that is releasably coupled to a first peg or pin 1092, a second peg or pin 1094 and to anchor guide eyelet 1011 in order to permit a two stage release of heart valve prosthesis 1000 (as shown in FIGS. 10A and 10B) and to permit an anchor tool 1060 to be guided there over (as shown in FIG. 10C). First and second pegs 1092, 1094 are attached to radially extend from an exterior of a distal end 1035 of inner shaft assembly 1034 and to be of a length that permits the first and second pegs 1092, 1094 to be slidable on an interior of delivery sheath assembly 1032. In a first stage of release, looped end 1090 of tether 1038 is coupled to first peg 1092 and second peg 1094 of inner shaft assembly 1034 after passing through crown 1007 and is trapped on the first and second pegs 1092, 1094 by distal end 1033 of delivery sheath assembly 1032 extending over the first and second pegs. At the first stage of release or deployment shown in FIG. 10A, a deployed position of heart valve prosthesis 1000 may be confirmed by fluoroscopy or other imaging technique. At the first stage of release if imaging shows the heart valve prosthesis to be improperly or poorly positioned at the implantation site, the tension may be adjusted or maintained on tether 1038 to permit recapture and/or repositioning of the heart valve prosthesis.

In a second stage of release, looped end 1090 of tether 1038 is released from first peg 1092 by the proximal retraction of delivery sheath assembly 1032 relative to inner shaft assembly 1034, and/or the distal advancement of the inner shaft assembly relative to the delivery sheath assembly. Upon release from first peg 1092, looped end 1090 of tether 1038 slides free of crown 1007 and thereafter catches on second peg 1094 of inner shaft assembly 1034 to remain trapped thereon by distal end 1033 of delivery sheath assembly 1032 extending over the second peg. The second stage of release shown in FIG. 10B permits a more controlled deployment of the inflow portion of heart valve prosthesis 1000, as the tether 1038 stops the self-expansion of frame 1010 at a second partial expansion or deployment state before a final release to full expansion of frame 1010 and full deployment of the heart valve prosthesis from delivery device 1030 is permitted to occur.

Figure 10D:
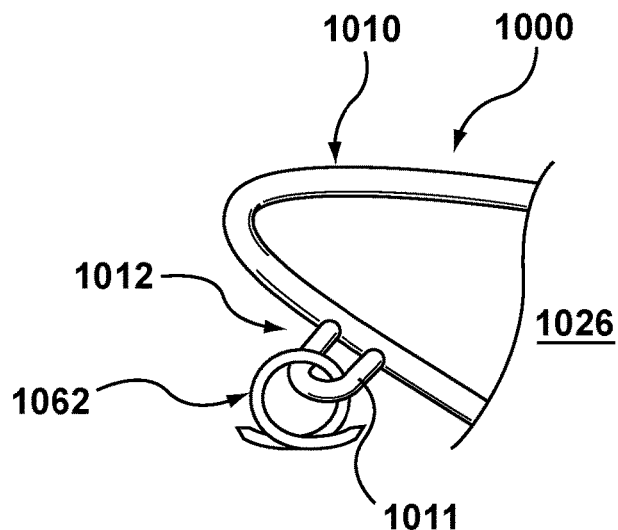

Upon continued proximal retraction of delivery sheath assembly 1032 relative to inner shaft assembly 1034 and/or continued distal advancement of the inner shaft assembly relative to the delivery sheath assembly, looped end 1090 of tether 1038 is released from second peg 1094 to permit full deployment of the heart valve prosthesis at the implantation site. As well upon release from second peg 1094, looped end 1090 of tether 1038 slides free of inner shaft assembly 1034 and thereafter catches on anchor guide eyelet 1011, as shown in FIG. 10C, such that heart valve prosthesis 1000 is no longer tethered to delivery device 1030. With tether 1038 decoupled from inner shaft assembly 1034, delivery device 1030 may be proximally removed from the patient with tether 1038 remaining proximally extending from anchor guide eyelet 1011. Proximally extending tether 1038 may then be used as an elongate guide member to permit an anchor tool 1060 to be tracked there over to anchor guide eyelet 1011, as shown in FIG. 10C. Anchor tool 1060 with anchor clip 1062 held in a straightened state within a distal end thereof is tracked to anchor guide eyelet 1062, and pusher rod 1066 is used to release the anchor clip from the anchor tool at the securement site to secure heart valve prosthesis 1000 to the heart. In an embodiment, as shown in FIG. 10D, anchor clip 1062 may be made to pass through and capture anchor guide eyelet 1011 of frame 1010 and tissue of the heart to secure heart valve prosthesis thereto. In another embodiment as similarly described with reference to the embodiment of FIGS. 8A-8C, anchor tool 1060 may be advanced along tether or elongate guide member 1038 until the anchor tool distal end contacts graft material 1026 of heart valve prosthesis 1000 such that when anchor clip 1062 is released therefrom, the anchor clip may be made to pass through the graft material of the prosthesis and tissue of the heart to secure the heart valve prosthesis thereto.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of implanting a heart valve prosthesis in a heart comprising:
   advancing a heart valve prosthesis having an anchor guide within one of a native heart valve or a previously implanted heart valve prosthesis, the anchor guide having an elongate guide member releasably secured thereto with an end or ends of the elongate guide member extending externally of the patient;
   deploying the heart valve prosthesis within the one of a native heart valve or a previously implanted heart valve prosthesis, wherein deploying the heart valve prosthesis includes controlling the release of tension on the elongate guide member to provide for a controlled release of the heart valve prosthesis during the step of deployment;
   imaging a location of the heart valve prosthesis to ascertain a position of the heart valve prosthesis at the one of a native heart valve or a previously implanted heart valve prosthesis prior to releasing all tension from the elongate guide member during the step of deploying;
   after deploying the heart valve prosthesis and imaging the location of the heart valve prosthesis, increasing tension on the elongate guide member to permit recapture or repositioning of the heart valve prosthesis when the step of imaging shows the heart valve prosthesis to be improperly positioned at the one of a native heart valve or a previously implanted heart valve prosthesis; and
   securing the heart valve prosthesis to the heart.

2. The method of claim 1, wherein securing the heart valve prosthesis to the heart further comprises:
   advancing an anchor tool having an anchor clip loaded therein along the elongate guide member to the anchor guide of the heart valve prosthesis;
   positioning the anchor tool at a securement site on the heart valve prosthesis; and
   releasing the anchor clip from the anchor tool at the securement site to secure the heart valve prosthesis to the heart.

3. The method of claim 2, wherein the step of positioning the anchor tool includes sliding the elongate guide member along the anchor guide to position the anchor tool at the securement site.

4. The method of claim 2 further comprising removing the anchor tool and the elongate guide member after the step of releasing the anchor clip.

5. The method of claim 1, wherein the anchor guide is a rail attached to one or both of a frame and a graft material of the heart valve prosthesis.

6. The method of claim 5, wherein the rail extends parallel to a strut of the frame with a first end attached adjacent to a crown of the frame and a second end attached along the strut.

7. The method of claim 6, wherein the rail is formed from a metallic material.

8. The method of claim 6, wherein the rail is formed from a biocompatible fabric that forms a belt-type loop.

9. The method of claim 8, wherein the first end of the belt-type loop is attached adjacent to the crown of the frame and the second end of the belt-type loop is attached to at least a graft material that covers the strut.

10. The method of claim 1, wherein the anchor guide is an eyelet disposed on a frame of the heart valve prosthesis that is attached to a strut of the frame at a spaced location from a crown of the frame.

11. A method of implanting a heart valve prosthesis in a heart comprising:
    loading a heart valve prosthesis having a plurality of anchor guides within a heart valve delivery device, wherein each of the plurality of anchor guides is releasably engaged by a respective elongate member of a plurality of elongate members and wherein tensioning of the plurality of elongate members aids in collapsing the heart valve prosthesis during loading, wherein each of the plurality of anchor guides is coupled to a different strut of a frame of the heart valve prosthesis, and wherein each of the plurality of anchor guides is a rail having a first end coupled to a strut of a frame of the heart valve prosthesis and a second end coupled to the strut, the rail forming a loop between the first end and the second end such that an elongate member of the plurality of elongated members extends between the anchor guide and the strut;
    advancing the heart valve delivery device to position the heart valve prosthesis at an implantation site within one of a native heart valve or a previously implanted heart valve prosthesis;
    deploying the heart valve prosthesis at the implantation site to include controlling the release of tension on the plurality of elongate members to provide for a controlled release of the heart valve prosthesis during deployment;
    imaging a location of the heart valve prosthesis to ascertain a position of the heart valve prosthesis at the implantation site prior to releasing all tension from the plurality of elongate members during the step of deploying;
    adjusting or maintaining tension on the plurality of elongate members to permit recapture or repositioning of the heart valve prosthesis when the step of imaging shows the heart valve prosthesis to be improperly positioned at the implantation site; and
    securing the heart valve prosthesis to the heart.

12. The method of claim 11, further comprising:
    advancing an anchor tool having an anchor clip loaded therein along an elongate member of the plurality of elongate members to a respective anchor guide associated therewith;
    positioning the anchor tool at a securement site on the heart valve prosthesis; and
    releasing the anchor clip from the anchor tool at the securement site to secure the heart valve prosthesis to the heart.

13. The method of claim 12, wherein the step of positioning the anchor tool includes sliding the elongate member along the respective anchor guide to position the anchor tool at the securement site.

14. The method of claim 12 further comprising removing the anchor tool and the plurality of elongate members after the step of releasing the anchor clip.

15. The method of claim 11, wherein each of the rails extends parallel to the strut of the frame with the first end attached adjacent to a crown of the frame and the second end attached along the strut.

16. The method of claim 15, wherein the rails are formed from a metallic material.

17. The method of claim 15, wherein each rail is formed from a biocompatible fabric that forms a belt-type loop.

18. The method of claim 17, wherein the first end of the belt-type loop forming each rail is attached adjacent to the crown of the frame and the second end of the belt-type loop forming each rail is attached to at least a graft material that covers the strut.

19. The method of claim 11, wherein each of the plurality of elongate members is disposed at a first end of its respective anchor guide adjacent to a respective crown of a frame of the heart valve prosthesis during at least the loading step and the deploying step.

* * * * *